(12) United States Patent
Khoury et al.

(10) Patent No.: US 11,040,071 B2
(45) Date of Patent: Jun. 22, 2021

(54) ANTI-ANGIOGENIC THERAPY BASED ON EXOSOMES DERIVED FROM MENSTRUAL STEM CELLS

(71) Applicant: Cells for Cells S.A., Santiago (CL)

(72) Inventors: Maroun Khoury, Santiago (CL); Francisca Alcayaga, Santiago (CL)

(73) Assignee: Cells for Cells S.A., Santiago (CL)

( * ) Notice: Subject to any disclaimer, the term of this patent is extended or adjusted under 35 U.S.C. 154(b) by 0 days.

(21) Appl. No.: 15/768,467

(22) PCT Filed: Oct. 13, 2016

(86) PCT No.: PCT/IB2016/056143
§ 371 (c)(1),
(2) Date: Apr. 13, 2018

(87) PCT Pub. No.: WO2017/064647
PCT Pub. Date: Apr. 20, 2017

(65) Prior Publication Data
US 2019/0038675 A1 Feb. 7, 2019

Related U.S. Application Data

(60) Provisional application No. 62/240,756, filed on Oct. 13, 2015.

(51) Int. Cl.
| | | |
|---|---|---|
| *A61P 13/08* | (2006.01) | |
| *A61K 35/12* | (2015.01) | |
| *A61K 35/28* | (2015.01) | |
| *A61K 35/14* | (2015.01) | |
| *A61K 31/704* | (2006.01) | |
| *A61K 31/675* | (2006.01) | |
| *C12N 5/0775* | (2010.01) | |
| *A61K 31/513* | (2006.01) | |
| *A61P 35/00* | (2006.01) | |
| *A61K 9/127* | (2006.01) | |
| *A61K 31/505* | (2006.01) | |

(52) U.S. Cl.
CPC ............ *A61K 35/28* (2013.01); *A61K 9/1271* (2013.01); *A61K 31/513* (2013.01); *A61K 31/675* (2013.01); *A61K 31/704* (2013.01); *A61K 35/12* (2013.01); *A61K 35/14* (2013.01); *A61P 35/00* (2018.01); *C12N 5/0665* (2013.01); *A61K 31/505* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 2013/0195899 A1* | 8/2013 | Ichim ................... | A61K 35/12 424/184.1 |
| 2013/0273011 A1 | 10/2013 | Ichim et al. | |
| 2014/0134626 A1 | 5/2014 | Ray et al. | |
| 2015/0157666 A1 | 6/2015 | Katakowski et al. | |
| 2015/0202248 A1 | 7/2015 | Bertino et al. | |

FOREIGN PATENT DOCUMENTS

WO 2012/087241 A1 6/2012

OTHER PUBLICATIONS

Meng et al., Endometrial regenerative cells: A novel stem cell population. Journal of Translational Medicine 2007, 5:57, p. 1-10 (Year: 2007).*
Linetai., Loss of mir-146a function in hormone-refractory prostate cancer. RNA (2008), 14:417-424. (Year: 2008).*
Lee et al. Exosomes Derived from Mesenchymal Stem Cells Suppress Angiogenesis by Down-Regulating VEGF Expression in Breast Cancer Cells. 2013. PLoS ONE 8(12): e84256. (Year: 2013).*
Alcayaga-Miranda et al., "Characterization of menstrual stem cells: angiogenic effect, migration. And hematopoietic stem cell support in comparison with bone marrow mesenchymal stem cells," *Stem Cell Research & Therapy* 6:32, 2015 (14 pages).
Beckermann et al., "VEGF expression by mesenchymal stem cells contributes to angiogenesis in pancreatic carcinoma," *British Journal of Cancer* 99:622-631, 2008.
Carmeliet, "Angiogenesis revisited: Principles and Strategies," AACR Special Conference: Tumor Angiogenesis and Vascular Normalization: Bench to Bedside to Biomarkers, Orlando Florida, Mar. 5-8, 2015 (4 pages)(abstract only).
Costa-Silva et al., "Pancreatic cancer exosomes initiate pre-metastatic niche formation in the liver," *Nat Cell Biol* 17(6):816-826, 2015 (HHS Public Access Author manuscript, available in PMC Jan. 16, 2018)(29 pages).
Ho et al., "Human Bone Marrow-Derived Mesenchymal Stem Cells Suppress Human Glioma Growth Through Inhibition of Angiogenesis," *Stem Cells* 31:146-155, 2013.

(Continued)

*Primary Examiner* — Arthur S Leonard
(74) *Attorney, Agent, or Firm* — Hamre, Schumann, Mueller & Larson, P.C.

(57) ABSTRACT

The present invention offers a solution to the lack of an effective alternative method to those already known to treat angiogenesis. In particular, the present invention is the first to show that a substantially pure population of exosomes derived from MenSCs have capacity to reduce tumor angiogenesis in diseases such as prostate cancer, breast cancer and pancreatic cancer. In this sense, the present invention shows that a substantially pure population of MenSCs-derived exosomes reduce the endogenous levels of reactive oxygen species (ROS) in cancer cells and the expression of pro-angiogenic factors such as VEGF, NF-KB, FGF and HIFα in the treated tumors. Overall, the invention offers a promising alternative method to treat angiogenesis. Since it is principally composed of exosomes produced by the Stem cells present in menstrual fluid, the invention provides an ease access and repeated sampling in a non-invasive manner. Such attributes allow the rapid production of the treatment.

6 Claims, 12 Drawing Sheets

Specification includes a Sequence Listing.

(56) References Cited

OTHER PUBLICATIONS

International Search Report and Written Opinion for International Application No. PCT/IB2016/056143, dated Mar. 17, 2017, 7 pages.

Kéramidas et al., "The dual effect of mesenchymal stem cells on tumour growth and tumour angiogenesis," *Stem Cell Research & Therapy* 4(2):41, 2013 (12 pages).

Khoury et al., "The promising potential of menstrual stem cells for antenatal diagnosis and cell therapy," *Frontiers in Immunology* 5(205):1-8, 2014.

Lin et al., "Exosomes from human adipose-derived mesenchymal stem cells promote migration through Wnt signaling pathway in a breast cancer cell model," *Mol Cell Biochem* 383:13-20, 2013.

Muhsin et al., "Bevacizumab," *Nature Reviews Drug Discovery* 3:995-996, 2004.

Orecchioni et al., "Complementary Populations of Human Adipose CD34+ Progenitor Cells Promote Growth, Angiogenesis, and Metastasis of Breast Cancer," *Cancer Res* 73(19):5880-5891, 2013 (13 pages).

Pepper, "Manipulating Angiogenesis. From Basic Science to the Bedside," *Arteriosclerosis, Thrombosis, and Vascular Biology* 17(4):605-619, 1997 (30 pages).

Urbich et al., "Role of microRNAs in vascular diseases, inflammation, and angiogenesis," *Cardiovascular Research* 79:581-588, 2008.

Vishnubhatla et al., "The Development of Stem Cell-derived Exosomes as a Cell-free Regenerative Medicine," *J Circ Biomark* 3(2):1-14, 2014.

Zhang et al., "Bone marrow-derived mesenchymal stem cells promote growth and angiogenesis of breast and prostate tumors," *Stem Cell Research & Therapy* 4(3):70, 2013, (15 pages).

Zhu et al., "Exosomes derived from human bone marrow mesenchymal stem cells promote tumor growth in vivo," *Cancer Letters* 315:28-37, 2012.

\* cited by examiner (A)

(B)

(C)

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: VEGF-A forward primer

<400> SEQUENCE: 1
acacattgtt ggaagcagcc c                                       21

<210> SEQ ID NO 2
<211> LENGTH: 24
<212> TYPE: DNA
<213> ORGANISM: Artificial Sequence
<220> FEATURE:
<223> OTHER INFORMATION: VEGF-A reverse primer

<400> SEQUENCE: 2
aggaaggtca accactcaca caca                                    24

<210> SEQ ID NO 3
<211> LENGTH: 21
<212> TYPE: DNA
<213> ORGANISM: Artificial Sequence
<220> FEATURE:
<223> OTHER INFORMATION: bFGF forward primer

<400> SEQUENCE: 3
agaagagcga ccctcacatc a                                       21

<210> SEQ ID NO 4
<211> LENGTH: 21
<212> TYPE: DNA
<213> ORGANISM: Artificial Sequence
<220> FEATURE:
<223> OTHER INFORMATION: bFGF reverse primer

<400> SEQUENCE: 4
```

```
cggttagcac acactcctttg                                                21

<210> SEQ ID NO 5
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 5
ggtctcctct gacttgaaca                                                 20

<210> SEQ ID NO 6
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 6
gtgagggtct ctctcttcct                                                 20
```

ANTI-ANGIOGENIC THERAPY BASED ON EXOSOMES DERIVED FROM MENSTRUAL STEM CELLS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200276_402USPC_SEQUENCE_LISTING.txt. The text file is 1.5 KB, was created on Sep. 9, 2018, and is being submitted electronically via EFS-Web.

FIELD OF THE INVENTION

The present invention can be included in the field of new medical treatments, wherein specific organelles of specific cells are used for treating a given disease or disorder. In particular, a substantially pure population of exosomes from Menstrual Stem cells is used in the present invention to treat angiogenesis of different types of cancer.

BACKGROUND OF THE INVENTION

Angiogenesis, the growth of new blood vessels, plays a crucial role in numerous diseases, including cancer. Tumor vascularization allows for nutrient supply of growing tumors or of newly implanted tumoral cells. Therefore, tumor growth and metastasis depend on angiogenesis. In that sense, anti-angiogenic therapies have been developed to kill cancer cells by starvation. However, the success of the anti-angiogenic drugs is limited by intrinsic refractoriness and acquired resistance. New strategies are thus needed to block tumor angiogenesis via alternative mechanisms ("Angiogenesis revisited: Principles and strategies, Peter Carmeliet"; Special Conference: Tumor Angiogenesis and Vascular 2015; DOI: 10.1158/1538-8514.TUMANG15-IA23).

Interestingly, Bone marrow mesenchymal stem cells (BMSCs) have shown anti-angiogenic properties. ("The dual effect of mesenchymal stem cells on tumour growth, tumour angiogenesis". Keramidas M et al., Stem cell research & therapy. 2013; "Human bone marrow-derived mesenchymal stem cells suppress human glioma growth through inhibition of angiogenesis". Ho I A et al., Stem cells 2013). However, BMSCs were also shown to support angiogenesis ("Bone marrow-derived mesenchymal stem cells promote growth, angiogenesis of breast and prostate tumors". Zhang T et al, Stem cell research & therapy. 2013; "VEGF expression by mesenchymal stem cells contributes to angiogenesis in pancreatic carcinoma". Beckermann B M et al., British journal of cancer 2008) as well as Human adipose CD34+ progenitor cells ("Complementary populations of human adipose CD34+ progenitor cells promote growth, angiogenesis, and metastasis of breast cancer". Orecchioni S et al., Cancer research. 2013). This dual effect in angiogenesis might be explained by the evidence that cells from different tissues have different properties and their effect on tumors might vary as well with the tumor cell type, its microenvironment and with the interaction with the tumoral cell.

Exosomes are small vesicles (30-200 nm) that originate when the inward budding of endosomal membrane forms Multivesicular bodies (MVBs) of almost all cell types and tumors. Exosomes are released into the extracellular space when the MVBs fuse with the plasma membrane. They are emerging as key mediators in intercellular communications through horizontal transfer of information via their molecular cargo, which includes proteins, DNAs, mRNAs and miRNAs that could trigger specific intracellular cascades that affect the gene expression of the recipient cells ("Pancreatic cancer exosomes initiate premetastatic niche formation in the liver". Costa-Silva B et al., Nature cell biology 2015; "Role of microRNAs in vascular diseases, inflammation, and angiogenesis". Urbich C. et al., Cardiovascular research 2008). In that regard, exosomes from human adipose-derived mesenchymal stem cells were shown to promote tumor cell migration in a breast cancer model ("Exosomes from human adipose-derived mesenchymal stem cells promote migration through Wnt signaling pathway in a breast cancer cell model". Ruizhu Lin et. al, Molecular and Cellular Biochemistry 2013). Moreover, it was reported that exosomes derived from bone marrow MSCs (BMSCs) have pro-angiogenic capacities in cancer cells by enhancing the expression of Vascular endothelial growth factor (VEGF), a potent angiogenic factor, through the activation of the ERK 1/2 pathway ("Exosomes derived from human bone marrow mesenchymal stem cells promote tumor growth in vivo". Zhu W et al., Cancer letters 2012). However, exosomes from BMSCs have also been shown to exert anti-angiogenic properties in 4T1 breast cancer cells ("Exosomes derived from human bone marrow mesenchymal stem cells promote tumor growth in vivo". Zhu W et al., Cancer letters 2012). In the aforesaid publication, the authors show that the addition of BMSCs exosomes to the culture media of 4T1 cells reduces the expression of VEGF through a mechanism at least partially mediated by miR-16, which is present in the BMSCs exosomes, and can be transfected into the 4T1 cells to target VEGF mRNA. In addition, in said publication in vitro and in vivo experiments also confirmed the anti-angiogenic capacity of BMSCs derived exosomes in 4T1 breast cancer cells.

Therefore, it seems clear that exosomes derived from BMSCs can have a dual effect on tumor angiogenesis. Since other studies have reported that BMSCs have this dual function in angiogenesis as well ("Bone marrow-derived mesenchymal stem cells promote growth, angiogenesis of breast and prostate tumors". Zhang T. et al., Stem cell research & therapy 2013; "VEGF expression by mesenchymal stem cells contributes to angiogenesis in pancreatic carcinoma". Beckermann B M et al., British journal of cancer 2008; "The dual effect of mesenchymal stem cells on tumour growth, tumour angiogenesis". Keramidas M et al., Stem cell research & therapy 2013; "Human bone marrow-derived mesenchymal stem cells suppress human glioma growth through inhibition of angiogenesis". Ho I A et al., Stem cells 2013), one could think that the role of exosomes in angiogenesis can be predicted from the role in angiogenesis of the cell that generates them.

Physiological angiogenesis occurs mainly during the female reproductive cycle ("Manipulating angiogenesis. From basic science to the bedside". Pepper M S. Arteriosclerosis, thrombosis, and vascular biology 1997). In this sense, stem cells derived from the menstrual fluid (MenSCs) have been related with pro-angiogenic capacities. More specifically, MenSCs were shown to be even more pro-angiogenic than BMSCs. Insertion of MenSCs in immunocompromised mice increased the number of blood vessels surrounding the inserted plug, which correlated with a significant increase in hemoglobin content, compared to insertion of BMSC or to controls. Additionally, MenSCs showed significantly higher levels of bFGF in comparison with BMSCs. ("Characterization of menstrual stem cells:

angiogenic effect, migration, hematopoietic stem cell support in comparison with bone marrow mesenchymal stem cells". Alcayaga-Miranda F et al., Stem cell research & therapy. 2015). One would then predict that, if any, exosomes derived from MenSCs would have pro-angiogenic capacities. Yet, in the present invention, the inventors find that exosomes derived from MenSCs, have anti-angiogenic capacities. Both in in vitro and in in vivo experiments they show that exosomes from the MenSCs reduce the levels of several pro-angiogenic parameters in different types of cancer, including prostate cancer, breast cancer and pancreatic cancer.

To the best of our knowledge, this is the first time that such function is shown to be related with MenSCs exosomes.

BRIEF DESCRIPTION

The present invention offers a solution to the lack of an effective alternative method to those already known to treat angiogenesis. In particular, the present invention is the first to show that a substantially pure population of exosomes derived from MenSCs have capacity to reduce tumor angiogenesis in diseases such as prostate cancer, breast cancer and pancreatic cancer. In this sense, the present invention shows that a substantially pure population of MenSCs-derived exosomes reduce the endogenous levels of reactive oxygen species (ROS) in cancer cells and the expression of pro-angiogenic factors such as VEGF, NF-κB, FGF and HIFα in the treated tumors. In addition, in vivo experiments with mice included in the present invention, show a decrease angiogenic capacity of tumors treated with MenSCs exosomes. Therefore, a substantially pure population of MenSCs-derived exosomes have an anti-angiogenic effect as shown both in the in vitro and in vivo experiments illustrated through-out the present specification. Overall, the invention offers a promising alternative method to treat angiogenesis. Since it is principally composed of exosomes produced by the stem cells present in menstrual fluid, the invention provides an ease access and repeated sampling in a non-invasive manner. Such attributes allow the rapid production of the treatment.

BRIEF DESCRIPTION OF THE FIGURES

It will be appreciated that the figures are not necessarily to scale, with emphasis instead being placed on illustrating the various aspects and features of embodiments of the invention, in which.

Stem cells isolated from the menstrual fluid were characterized according to ISCT guidelines. A. MenSCs showed stem cell-like immunophenotypic markers. FACS profile of a representative MenSCs sample. Red filled histograms denote the fluorescent profile of the indicated antigens and light-blue filled histograms correspond to isotype-matched controls. B. MenSCs displayed mesodermal differentiation. Tri-lineage differentiation of a representative MenSCs sample. Cells were cultured with adipogenic, osteogenic and chondrogenic induction media for 14-21 days and then stained with Oil Red O, Alizarin Red and Safranin O staining, respectively. Abbreviations: MenSCs, menstrual derived mesenchymal stem cells; ISCT, international society of cellular therapy. Scale Bar: 200 µm

Exosomes were purified from the conditioned media of MenSCs using differential centrifugation. A. Electron microscopy micrographs of exosomes isolated from MenSCs cell culture conditioned media. Scale Bar: 100 nm. B. Particle size by nanoparticle tracking analysis for MenSCs-secreted exosomes. Data are presented as mode values±SE C. Western blot analysis of exosomes and cell lysates. 15 µg of proteins were loaded per lane. Abbreviations: MenSCs, menstrual derived mesenchymal stem cells; Exo, exosomes; CL, cell lysates; nm, nanometers; µg, micrograms; ml, milliliters; SE, standard error.

Figure 3:
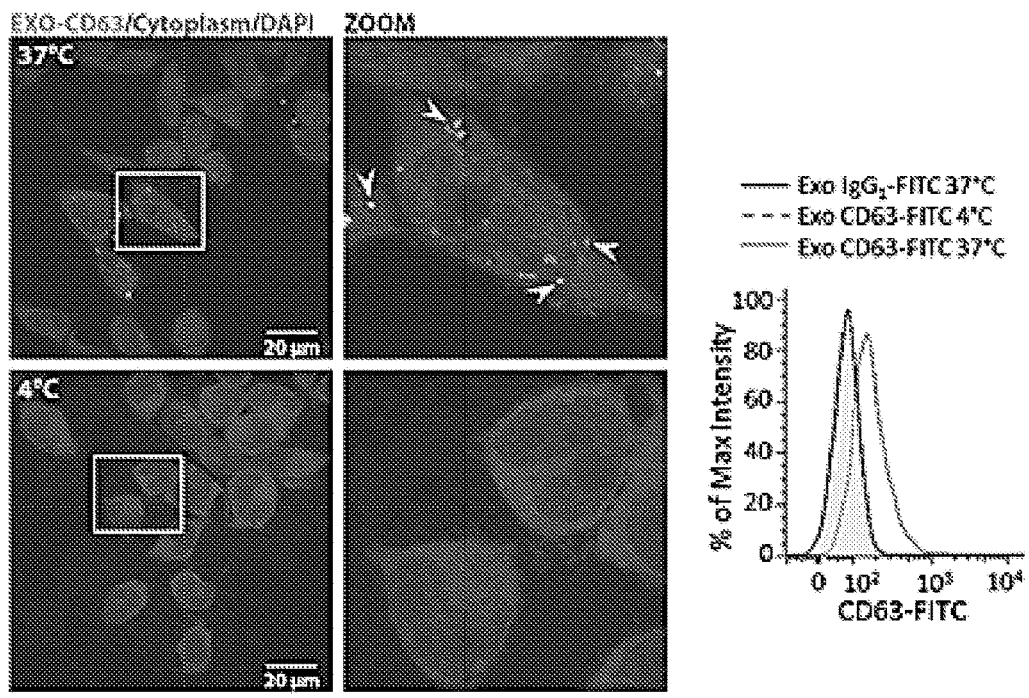

FIG. 3 shows the uptake of exosomes by tumor cells.

PC3 cells were incubated with immuno-labeled MenSCs-derived exosomes (20 µg) for 3 hours at either 37° C. or 4° C. and uptake of exosomes by PC3 cells was assessed. Exosomes internalization (white arrows) was visualized with confocal microscopy (left panel) and flow cytometry (right panel).

Figure 4:
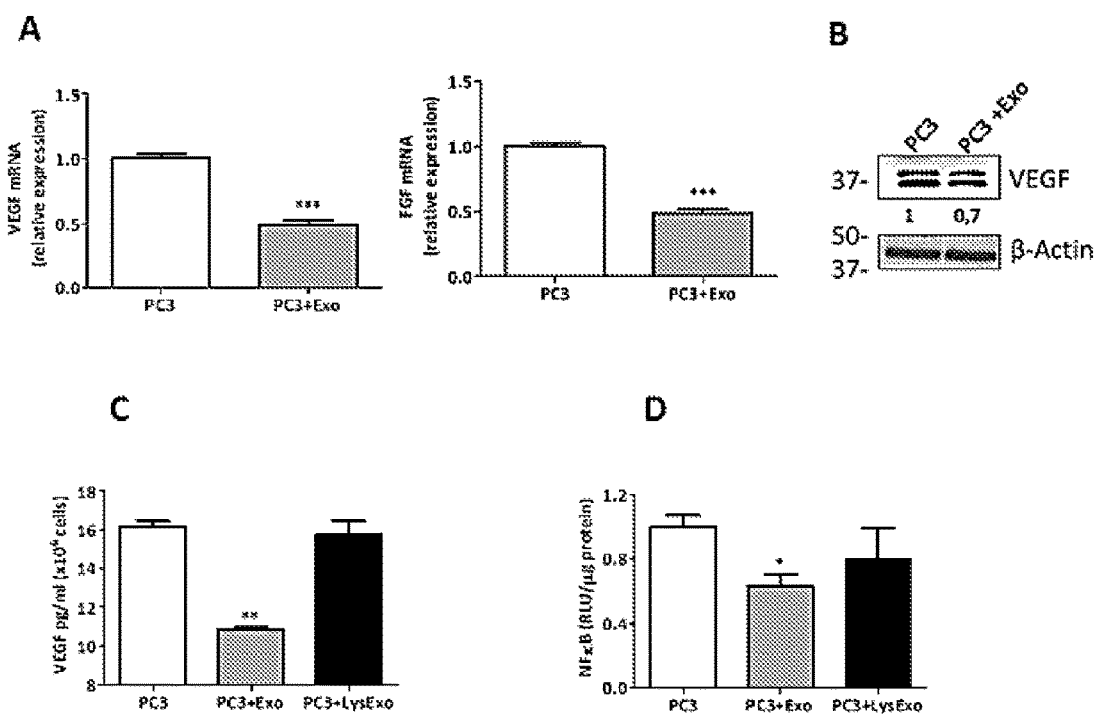

FIG. 4 shows how MenSCs-derived exosomes downregulate VEGF, FGF expression and NF-κB activity.

PC3 cells were incubated in the absence or presence of MenSCs-derived exosomes or lysed exosomes for 36 hours and their effects on VEGF, FGF and NF-κB were determined. Relative expression level of VEGF and FGF were assessed by qRT-PCR (A); Protein level of VEGF was determined by western-blot (B); VEGF secretion was measured by ELISA (C); NF-κB activity was assessed by luciferase reporter assay (D). Data are presented as mean values±SE. Western blotting results were evaluated by densitometry, corrected with respect to β-actin expression, and expressed relative to the value obtained with the corresponding control (arbitrarily set as 1). Equal protein loading was assessed by anti-β-actin immunoblotting. Abbreviations: MenSCs, menstrual derived mesenchymal stem cells; Exo, exosomes; LysExo, lysed exosomes; VEGF, vascular endothelial growth factor; FGF, fibroblast growth factor; NF-κB, nuclear factor-kappa B; SE, standard error.

Figure 5:
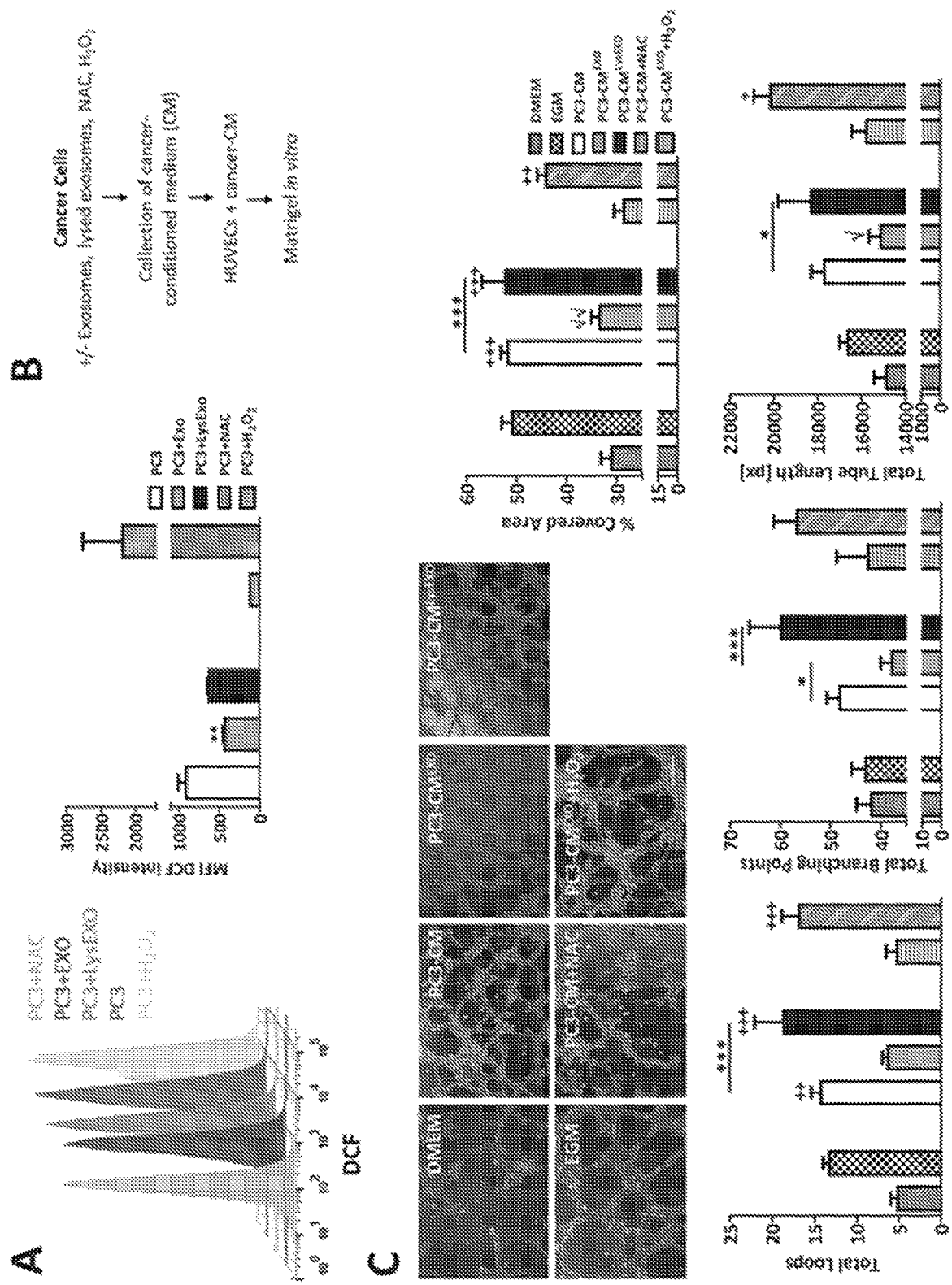

FIG. 5 shows how the inhibition of ROS by MenSCs-derived exosomes reduce angiogenesis in vitro.

A. PC3 cells were treated with or without exosomes or lysed exosomes and assayed for ROS production by FACS using the fluorescent dye DCFDA. NAC and H2O2 were used as negative and positive control, respectively. Representative histograms show ROS generation in each experimental condition. Graph represents the mean values±SE of the MFI of DCF. *, respect to PC3. B-C. HUVEC were resuspended in the CM derived from PC3 cells treated with exosomes, exosomes plus H2O2, lysed exosomes, NAC, or untreated, and seeded in matrigel (B); Representative images show tube formation after 5 hours. Graphs represent the quantitative analysis of the angiogenic potential (C). Scale bar: 200 µm. *, respect to PC3-CMEXO; √, respect to PC3-CMEXO+H2O2; +, respect to PC3-CM+NAC. Abbreviations: MenSCs, menstrual derived mesenchymal stem cells; EXO, exosomes; CM, conditioned medium; LysEXO, lysed exosomes; DMEM, Dulbecco's modified Eagle's medium; EGM, endothelial growth medium; NAC, N-acetylcysteine; ROS, reactive oxygen species; DCFDA, 2', 7'-dichlorofluorescin diacetate; DCF, 2', 7'-dichlorofluorescin; FACS, fluorescence-activated cell sorting; MFI, mean fluorescent intensity; SE, standard error.

Figure 6:
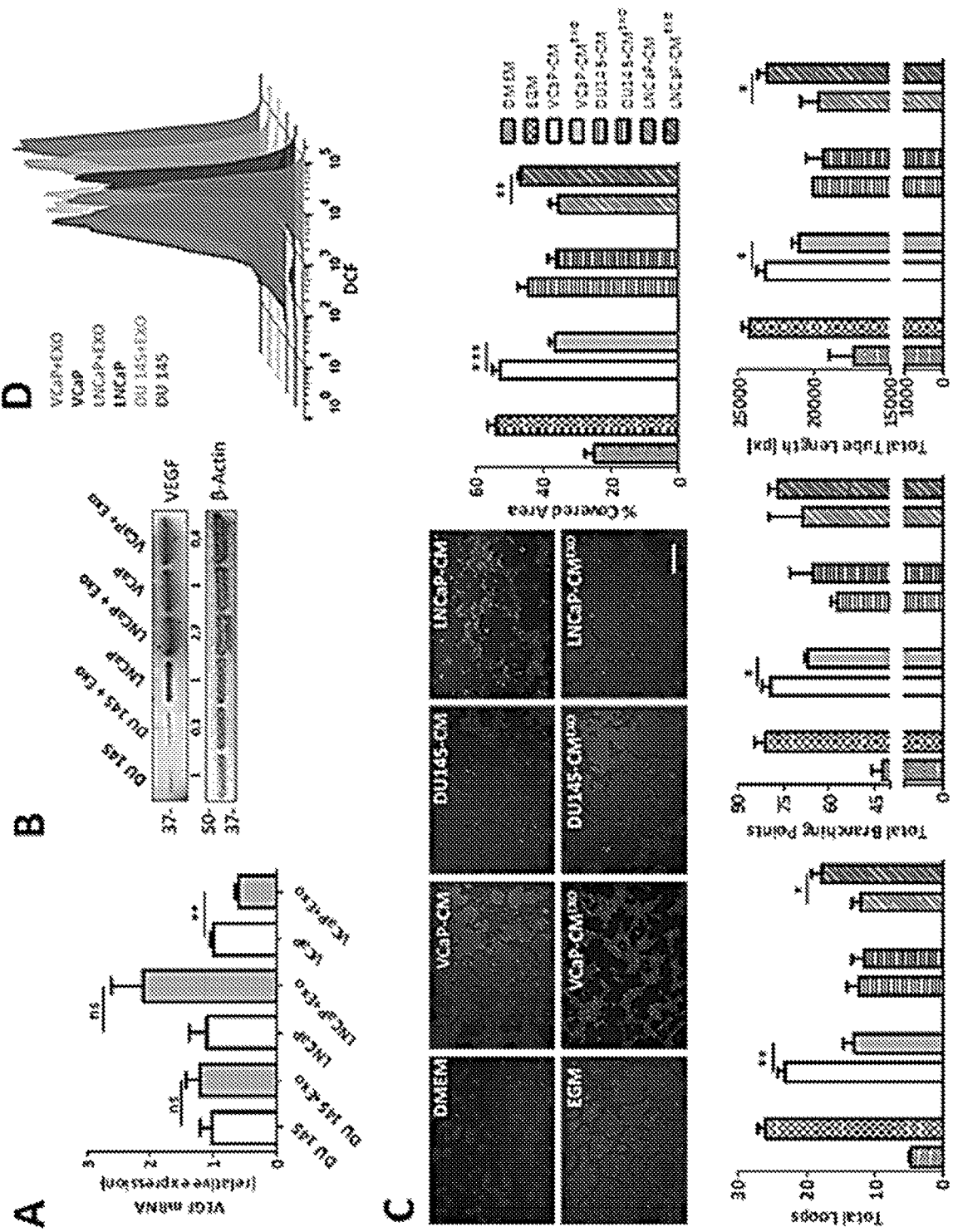

FIG. 6 shows that MenSCs-derived exosomes have an ant-angiogenic effect in PC3 and VcaP cells.

A panel of prostate cancer cell lines were incubated in the absence or presence of MenSCs-derived exosomes for 36 hours and their effect on VEGF, tube-like structures formation and ROS was determined. Relative expression levels of VEGF was assessed by qRT-PCR (A); Protein level of VEGF was determined by western-blot (B); Representative images show tube formation after 5 hours. Graphs represent the quantitative analysis of the angiogenic potential (C); ROS generation by FACS using the fluorescent dye DCFDA (D). Data are presented as mean values±SE. Western blotting results were evaluated by densitometry, corrected with respect to β-actin expression, and expressed relative to the value obtained with the corresponding control (arbitrarily set as 1). Equal protein loading was assessed by anti-β-actin immunoblotting. Scale bar: 200 μm. Abbreviations: MenSCs, menstrual derived mesenchymal stem cells; EXO, exosomes; CM, conditioned medium; LysEXO, lysed exosomes; DMEM, Dulbecco's modified Eagle's medium; EGM, endothelial growth medium; NAC, N-acetylcysteine; ROS, reactive oxygen species; DCFDA, 2', 7'-dichlorofluorescin diacetate; DCF, 2', 7'-dichlorofluorescin; FACS, fluorescence-activated cell sorting; MFI, mean fluorescent intensity; SE, standard error.

Figure 7:
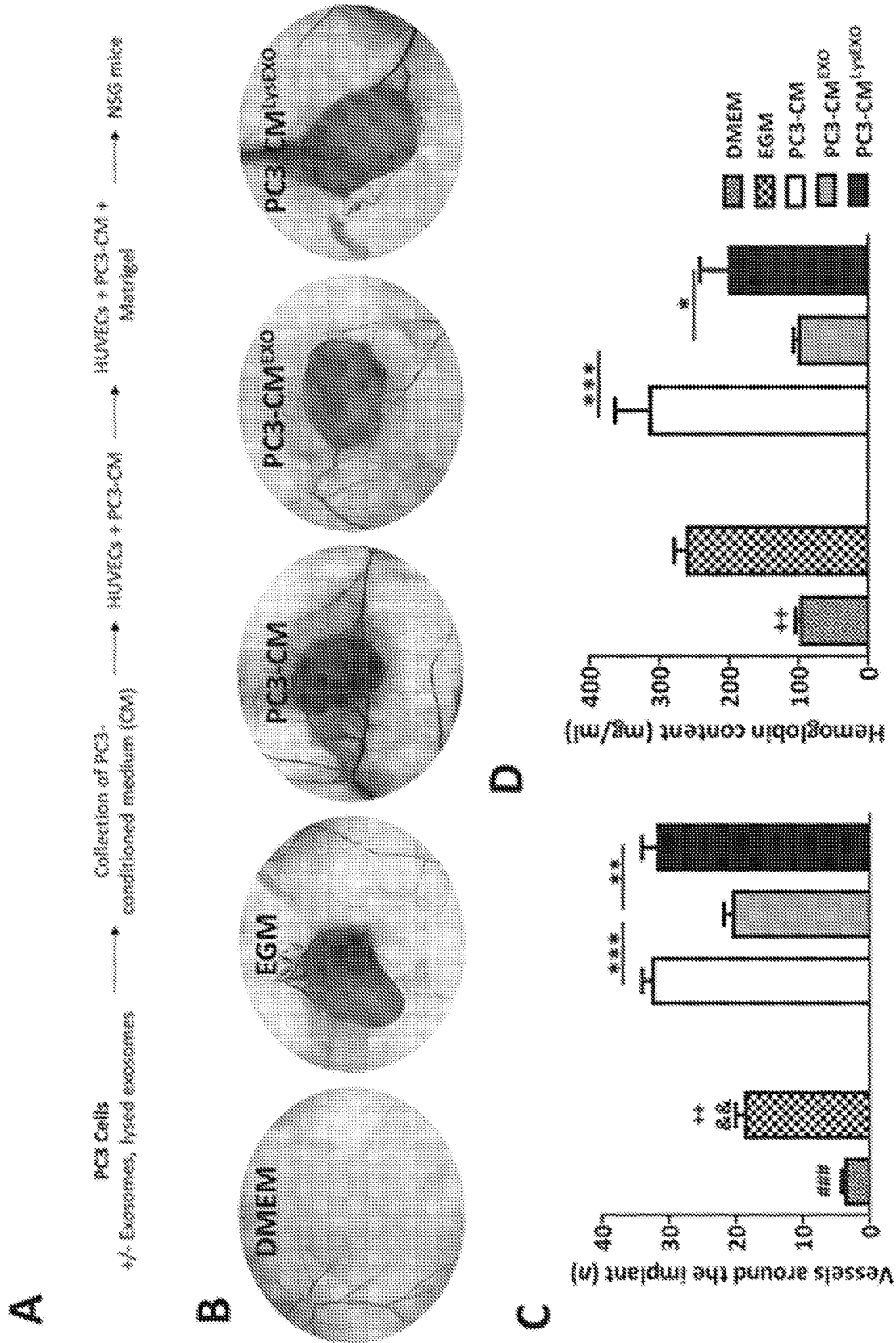

FIG. 7 shows that MenSCs-derived exosomes inhibit angiogenesis in vivo.

PC3 cells were incubated in absence or presence of exosomes or lysed exosomes for 36 hours and the CM was collected and mixed with HUVEC cells in matrigel to perform the angiogenesis assay in vivo (PC3-CM, n=8; PC3-CMEXO, n=8; PC3-CMLysEXO, n=6). The matrigel mixed with DMEM (n=4) or EGM (n=4) were used as negative and positive control, respectively. A. Diagram of the experimental design. B. Representative images of matrigel in NSG mice. C. Quantification of blood vessels around the matrigel implants. D. Hemoglobin content of the matrigel implants. Data represent mean±SE. Scale bar: 200 μm. Abbreviations: MenSCs, menstrual derived mesenchymal stem cells; EXO, exosomes; CM, conditioned medium; LysEXO, lysed exosomes; DMEM, Dulbecco's modified Eagle's medium; EGM, endothelial growth medium; NSG, NOD scid gamma.

Figure 8:
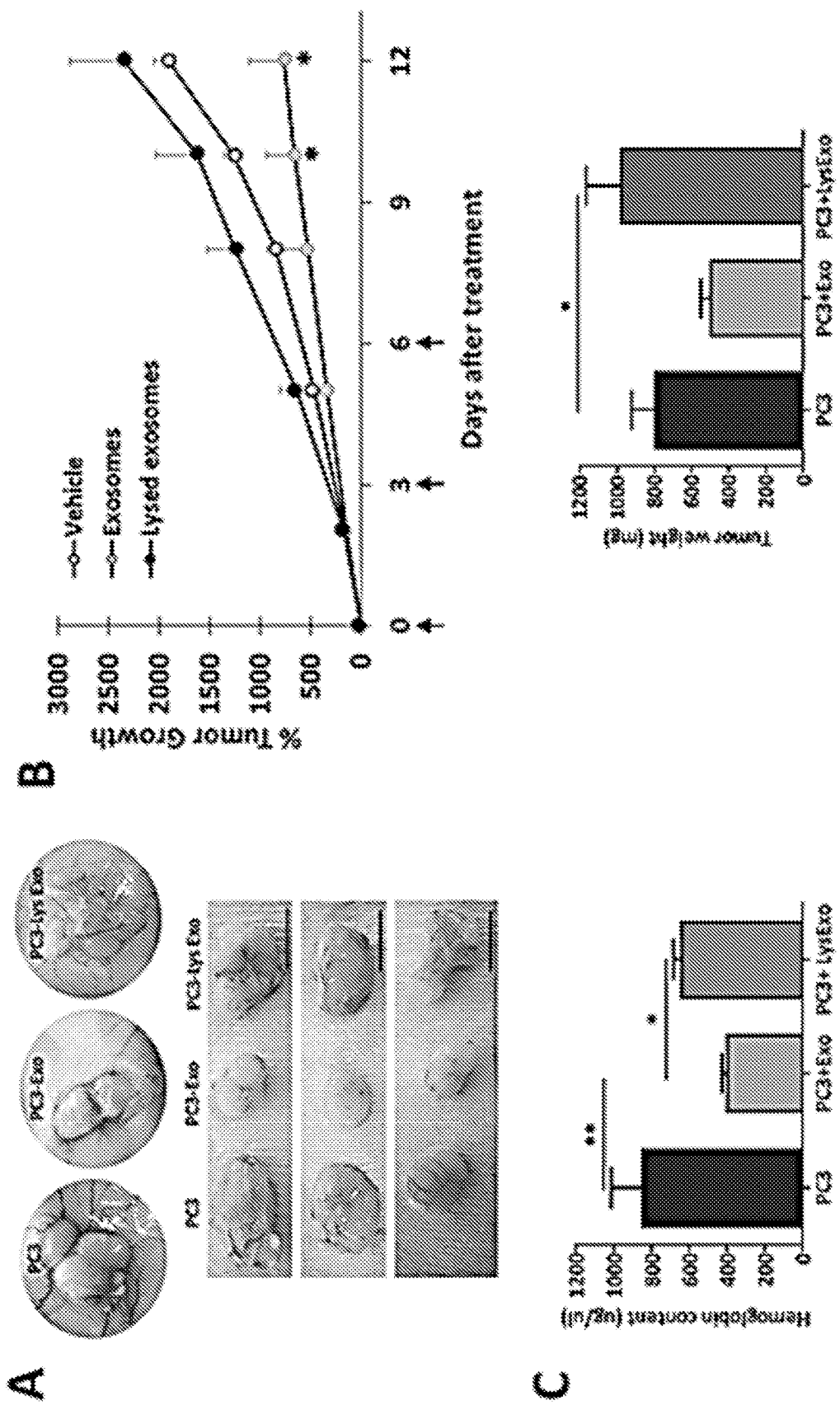
Figure 8:
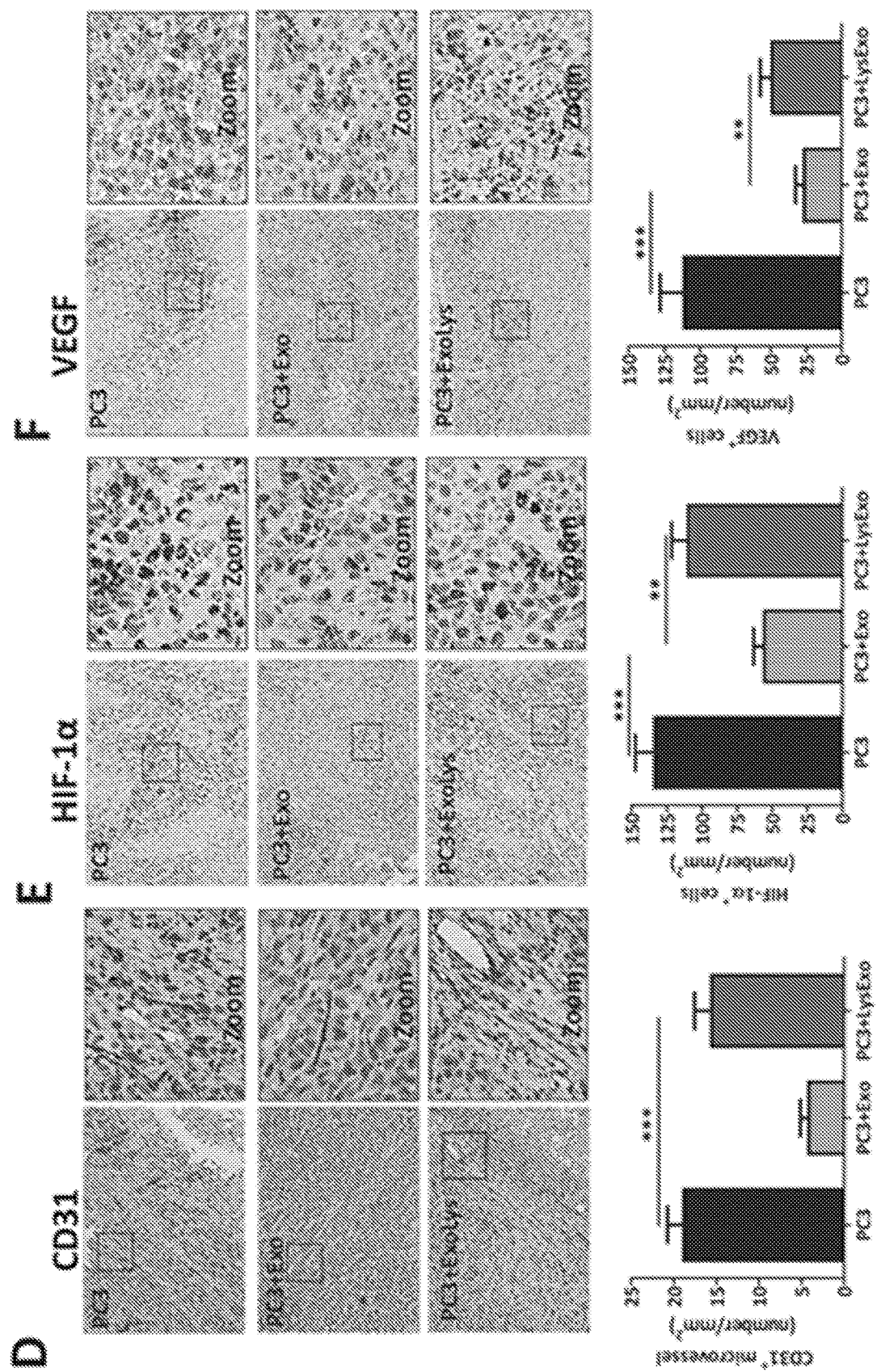

FIG. 8 shows that MenSCs-derived exosomes decrease angiogenesis and tumor growth in vivo.

PC3 cells (1.5×106) were implanted subcutaneously in mice and when the tumor volume reached ~80 mm3, three injections of exosomes (n=12), lysed exosomes (n=8), and vehicle (n=14) were performed at defined time points (arrows in B). A. Representative images of tumors after treatments. Scale bar: 1 cm; B. Percentage of tumor growth and weight at day 12 after treatment; C. Hemoglobin content of the tumor tissue. D-F. CD31, HIF-1α and VEGF immunohistochemical staining and quantification. Images are shown at 40×. Data are presented as mean values±SE. Abbreviations: MenSCs, menstrual derived mesenchymal stem cells; EXO, exosomes; LysEXO, lysed exosomes; VEGF, vascular endothelial growth factor; HIF-1α, hypoxia-inducible factor 1; SE, error standard.

Figure 9:
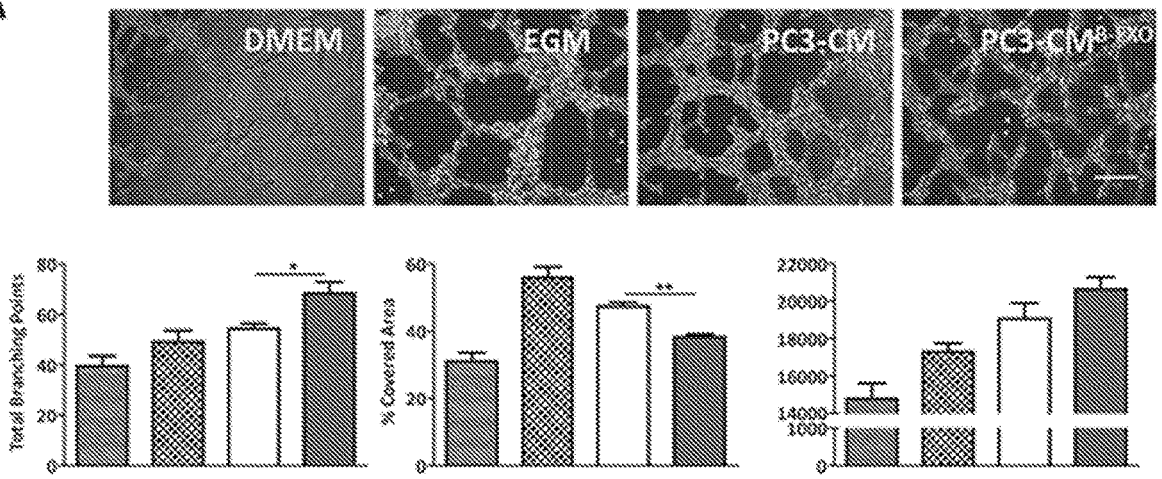
Figure 9:
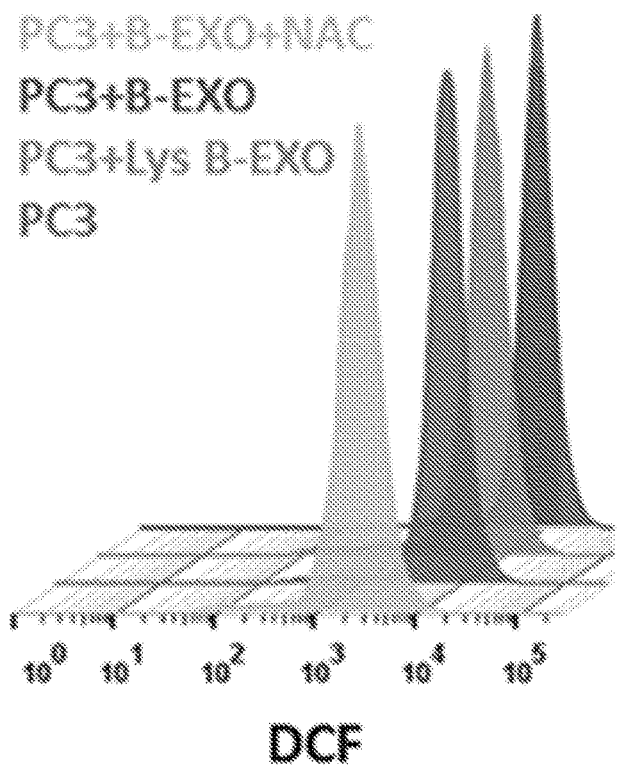

FIG. 9 shows that BMSCs-derived exosomes increase tumor angiogenesis in vitro.

A. HUVECs were resuspended in CM from PC3 cells treated with BMSC-derived exosomes or untreated, and seeded in matrigel. Representative images show tube formation after 5 hours. Graphs represent quantitative analysis of the angiogenic potential. Data are presented as mean values±SE. B. PC3 cells were treated with or without BMSC-derived exosomes or lysed exosomes, and assayed for ROS production by FACS using the fluorescent dye DCFDA. Representative histograms show endogenous ROS production in each experimental condition. Data are presented as mean values±SE. Scale bar: 200 μm. Abbreviations: BMSCs, bone marrow derived mesenchymal stem cells; EXO, exosomes; CM, conditioned medium; DMEM, Dulbecco's modified Eagle's medium; EGM, endothelial growth medium; ROS, reactive oxygen species; NAC, N-acetylcysteine; DCFDA, 2', 7'-dichlorofluorescein diacetate; DCF, 2', 7'-dichlorofluorescein; FACS, fluorescence-activated cell sorting; SE, standard error.

Figure 10:
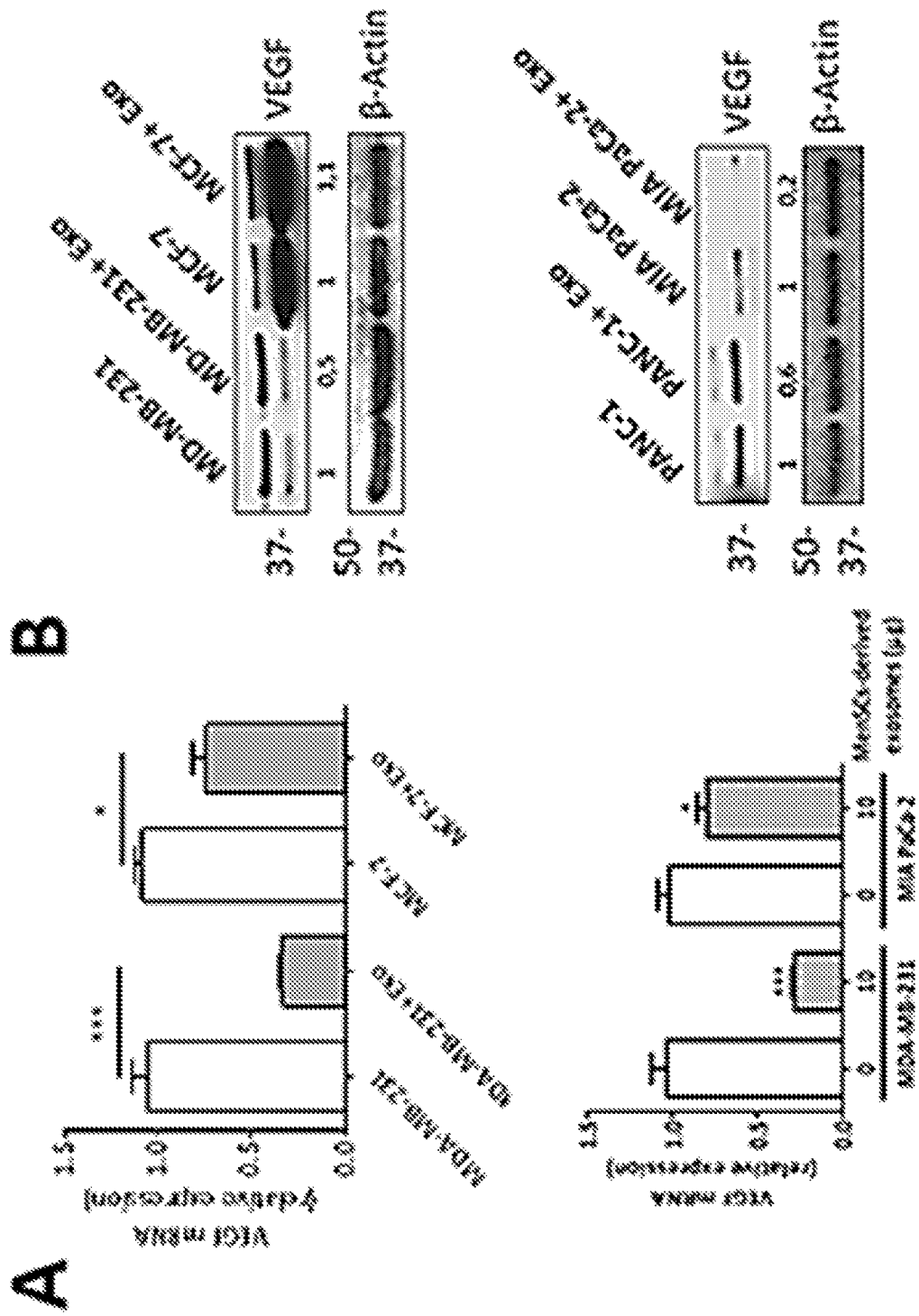
Figure 10:
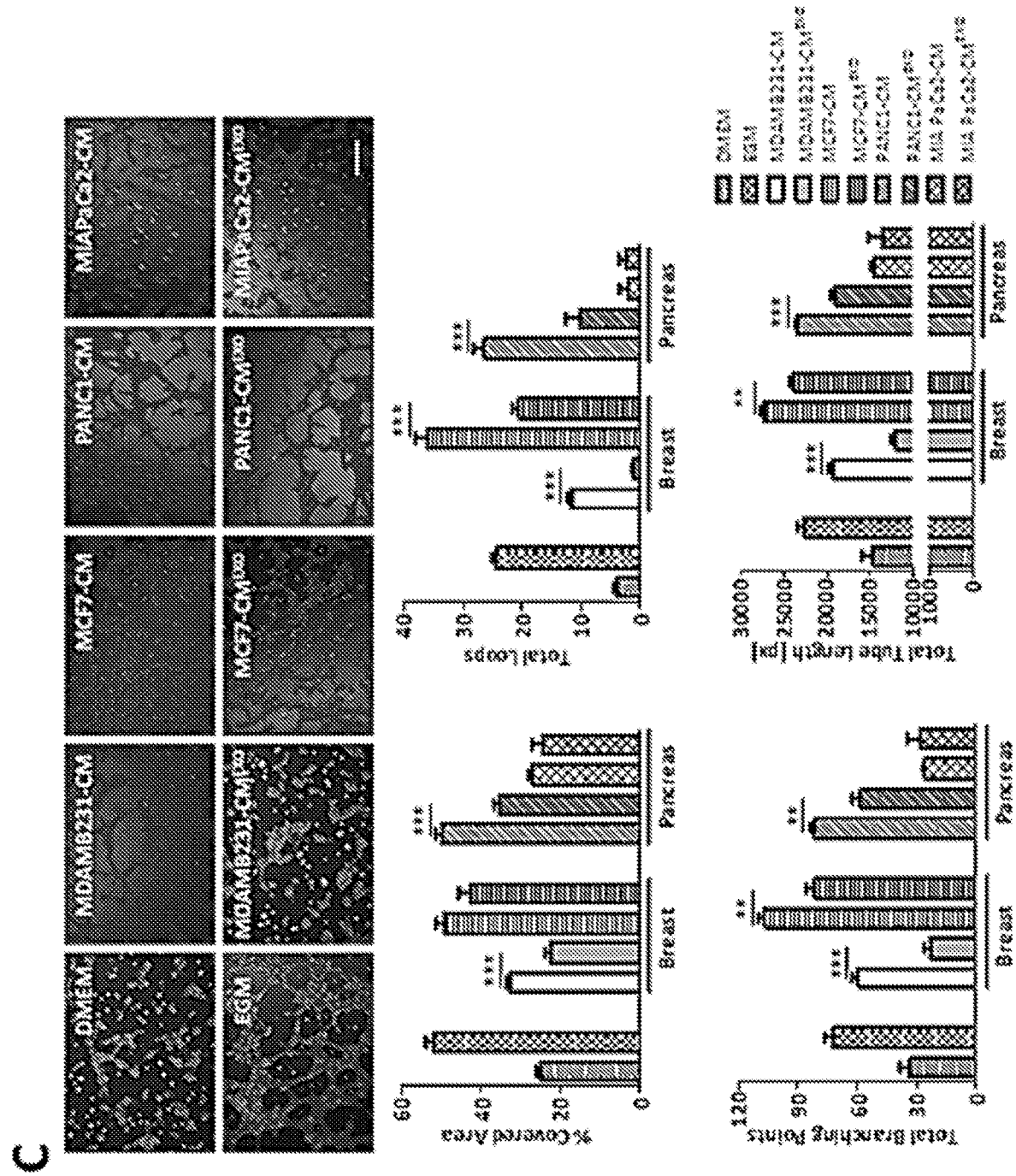
Figure 10:
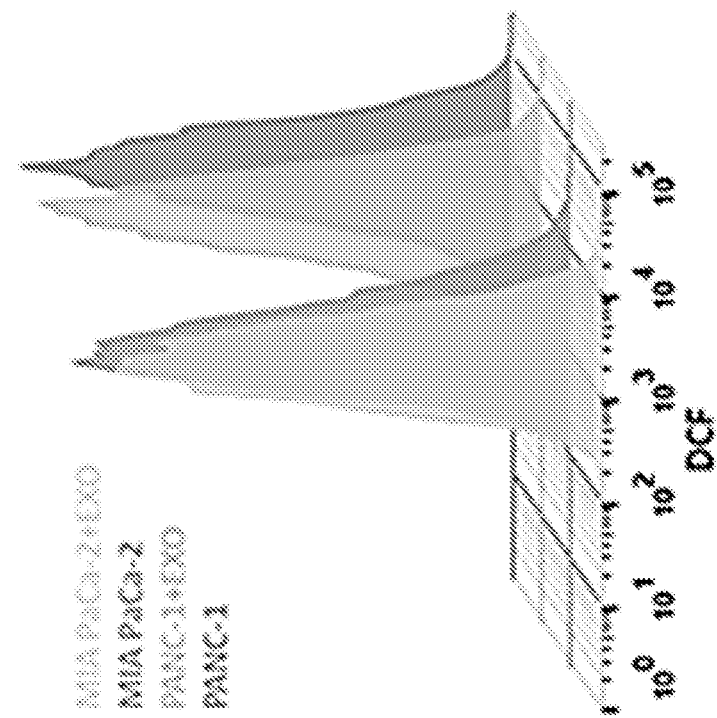
Figure 10:
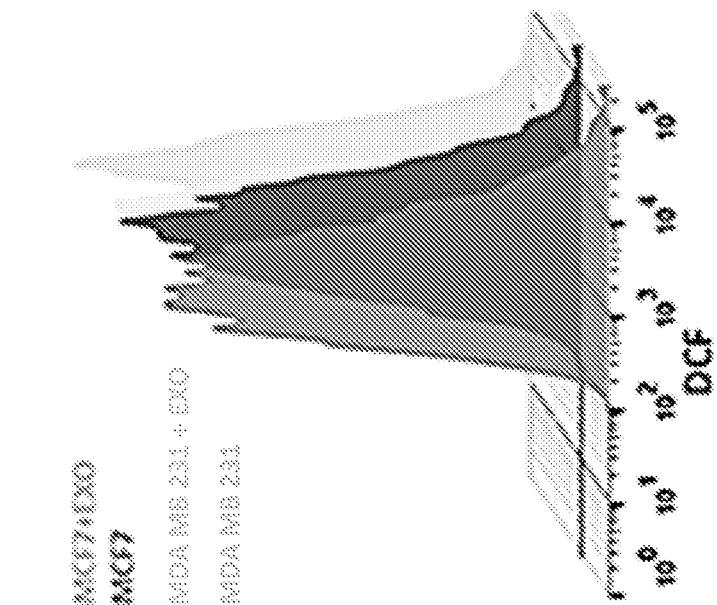

FIG. 10 shows that MenSCs-derived exosomes inhibition of tumor angiogenesis is cancer cell-type dependent.

A-B. Breast (MDA-MB-231 and MCF-7) and pancreatic (MIA PaCa-2 and PANC-1) cancer cell lines were incubated in the absence or presence of MenSCs-derived exosomes for 36 hours and their effects on VEGF were determined. Relative expression levels of VEGF was assessed by qRT-PCR (A) and western-blot (B). C. HUVECs were resuspended in CM from tumor cells treated with MenSCs-derived exosomes or untreated, and seeded in matrigel. Representative images show tube formation after 5 hours. Graphs represent quantitative analysis of the angiogenic potential. Data are presented as mean values±SE. Western blot results were evaluated by densitometry, corrected with respect to β-actin expression, and expressed relative to the value obtained with the corresponding control (arbitrarily set as 1). Equal protein loading was assessed by anti-β-actin immunoblotting. Scale bar: 200 μm. D-E. Cancer cells were treated with or without MenSCs-derived exosomes and assayed for ROS production by FACS using the fluorescent dye DCFDA. Representative histograms show endogenous ROS production in each experimental condition. Abbreviations: EXO, exosomes; CM, conditioned medium; DMEM, Dulbecco's modified Eagle's medium; EGM, endothelial growth medium; ROS, reactive oxygen species; DCFDA, 2', 7'-dichlorofluorescein diacetate; DCF, 2',7'-dichlorofluorescein; FACS, fluorescence-activated cell sorting; ns, non-significant; SE, standard error.

DETAILED DESCRIPTION OF THE INVENTION

Definitions

In the context of the present invention, the term "angiogenesis" is understood as the growth of new blood vessels from pre-existing blood vessels. Without limiting the scope of the present invention, it is noted that the angiogenic capacity can be detected, among other methods, by the capacity of Human vein endothelial cells (HUVEC) to form tubule-like structures in a matrigel structure, the capacity to promote the formation of new blood vessels in vivo and by an increased concentration of pro-angiogenic factors selected from the list consisting of VEGF, FGF, HIF1α, or NFKB compared with a sample that does not have angiogenic capacities.

In the context of the present invention, the term "pro-angiogenic" is understood as the characteristic of a product that has the capacity to increase angiogenesis of the cells it targets.

In the context of the present invention, the term "anti-angiogenic" is understood as the characteristic of a product that has the capacity to decrease angiogenesis of the cells it targets.

In the context of the present invention, the term "Menstrual stem cells (MenSCs)" is understood as stem cells isolated from the menstrual fluid of woman that are in fertile ages. These cells show spindle-shape morphology, and stem cell-like phenotypic markers: MenSCs express CD105, CD44, CD73, CD90 and HLA-ABC, but show negative expression for CD45, CD34, CD14 and HLA-DR. They also show mesodermal lineage differentiation under specific protocols of the laboratory.

In the context of the present invention, "exosomes" refer to small vesicles (30-200 nm) that originate when the inward budding of endosomal membrane forms Multivesicular bodies (MVBs). Exosomes are released into the extracellular space when the MVBs fuse with the plasma membrane. They contain a specific molecular cargo, which comprising proteins, DNAs, mRNAs and miRNAs.

In the context of the present invention, "MenSCs-derived exosomes" refers to the exosomes produced by the MenSCs. They are isolated by a process of serial dilutions by centrifugation of the supernatant of the MenSCs culture, followed by two ultracentrifugations of the supernatant to save the pellet, which contains the exosomes.

In the context of the present invention, the term "conditioned media" is understood as the supernatant of cell cultures.

In the context of the present invention, the term "isolated" indicates that the exosomes or exosome population is not within the environment where it originated. The exosome or the population of exosomes has been substantially separated from surrounding environment. In some embodiments, the exosomes or exosome population is substantially pure or enriched if it was separated from surrounding environment and if the sample contains at least about 50%, at least about 55%, at least about 60%, at least about 70%, at least about 75%, in some embodiments at least about 85% in some embodiments at least about 90%, and in some embodiments at least 95% of exosomes. In other words, the sample is substantially pure or enriched if it was separated from the surrounding environment and if the sample contains less than about 50%, less than 40%, less than 30%, preferably less than 25%, in some embodiments less than about 15%, and in some embodiments less than about 5% of materials other than the exosomes. Such percentage values refer to percentage by weight or of a population of extracellular vesicles, wherein extracellular vesicles refer to membrane surrounded structures released by cells to the extracellular environment. They display diameters ranging from 20 nm to 5 µm, depending on their subtype. There are released by many cell types as a means of communicating with other cells and also potentially removing cell contents. The cargo of extracellular vesicles includes the proteins, lipids, nucleic acids, and membrane receptors of the cells from which they originate. The term isolated also encompasses exosomes which have been removed from the environment from which they originated. The term also encompasses exosomes which have been removed from the environment where they originated, and subsequently re-inserted into an organism. The organism which contains the re-inserted exosomes may be the same organism from which the cells that produced the exosomes originated, or it may be a different organism, i.e. a different individual of the same species.

In the context of the present invention, the term "VEGF" refers to VEGFA which is member of the Vascular endothelial growth factor (VEGF) family. VEGFA protein is often found as a disulfide linked homodimer. This protein is a glycosylated mitogen that specifically acts on endothelial cells and has various effects, including mediating increased vascular permeability, inducing angiogenesis, vasculogenesis and endothelial cell growth, promoting cell migration, and inhibiting apoptosis.

In the context of the present invention, the term "FGF" refers to FGF2, also known as bFGF, or FGF-β, which is a member of the fibroblast growth factor family. It binds heparin and has a broad range of cellular activities, including cell survival, division, differentiation and migration. FGF2 plays a key role in various processes, including limb and nervous system development, wound healing and tumor growth, as well as angiogenesis. It is expressed in normal ovarian tissue and in hepatocellular carcinoma, but not in normal liver cells. FGF2 interacts with FGF receptors FGFR1, -2, -3 and -4.

In the context of the present invention, the term "NFKappaB" refers to nuclear factor kappa-light-chain-enhancer of activated B cells. It is a protein complex that controls of DNA, cytokine production and cell survival. NF-κB is found in almost all animal cell types and is involved in cellular responses to stimuli such as stress, cytokines, free radicals, heavy metals, ultraviolet irradiation, oxidized LDL, and bacterial or viral antigens. NF-κB plays a key role in regulating the immune response to infection (κ light chains are critical components of immunoglobulins). Incorrect regulation of NF-κB has been linked to cancer, angiogenesis, inflammatory and autoimmune diseases, septic shock, viral infection, and improper immune development. NF-κB has also been implicated in processes of synaptic plasticity and memory.

In the context of the present invention, the term "HIF1 α" refers to Hypoxia-inducible factor 1-alpha, also known as HIF-1-alpha, is a subunit of a heterodimeric transcription factor hypoxia-inducible factor 1 (HIF-1). It is a basic helix-loop-helix PAS domain containing protein, and is considered as the master transcriptional regulator of cellular and developmental response to hypoxia. The dysregulation and overexpression of HIF1A by either hypoxia or genetic alternations have been heavily implicated in cancer biology, as well as a number of other patho-physiologies, specifically in areas of vascularization and angiogenesis, energy metabolism, cell survival, and tumor invasion.

In the context of the present invention, Reactive oxygen species (ROS) refer to chemically reactive chemical species containing oxygen. Examples include peroxides, superoxide, hydroxyl radical, and singlet oxygen. ROS are generated during mitochondrial oxidative metabolism as well as in cellular response to xenobiotics, cytokines, and bacterial invasion. Oxidative stress refers to the imbalance due to excess ROS or oxidants over the capability of the cell to mount an effective antioxidant response. Oxidative stress results in macromolecular damage and is implicated in various disease states such as atherosclerosis, diabetes, cancer, pathological angiogenesis, neurodegeneration, and aging.

Description

Menstrual Stem Cells (MenSCs) are stem cells obtained from the menstrual fluid of woman that are in fertile ages. These cells show spindle-shape morphology, and stem cell-like phenotypic markers: MenSCs express CD105, CD44, CD73, CD90 and HLA-ABC, but show negative expression for CD45, CD34, CD14 and HLA-DR. They also show mesodermal lineage differentiation under specific protocols of the laboratory.

They show the ability to differentiate into adipocytes, chondrocytes and osteoblast cells. This population of MenSCs, compared to the broadly studied bone marrow derived mesenchymal stem cells (BMSCs) out-performs bone marrow derived mesenchymal stem cells in proliferation rate and support of hematopoietic stem cells (HSCs) expansion in vitro.

Exosomes are small vesicles of 30 to 200 nm, preferably 30 to 150 nm, preferably 40 to 120 nm, more preferably between 50 and 100 nm in diameter that originate when the inward budding of endosomal membrane forms multivesicular bodies (MVBs) and are produced by almost all cell types and cancer cells. Exosomes are released into the extracellular space when the MVBs fuse with the plasma membrane. They are emerging as key mediators in intercellular communications through horizontal transfer of information via their molecular cargo, which includes proteins, DNAs, mRNAs and miRNAs that could trigger specific intracellular cascades that affect the gene expression of the recipient cells.

Figure 2:
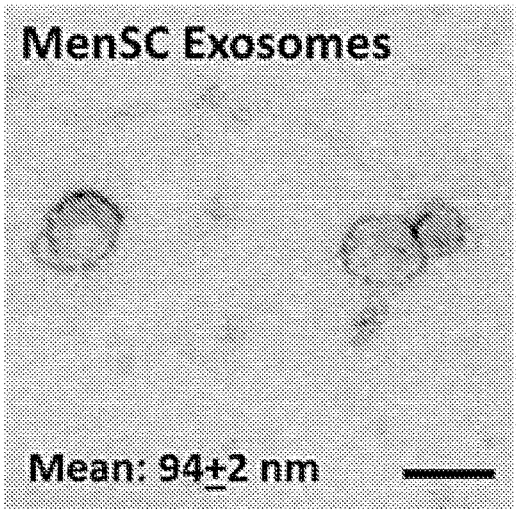
FIG. 2 shows the characterization of MenSCs-derived exosomes.
Figure 2:
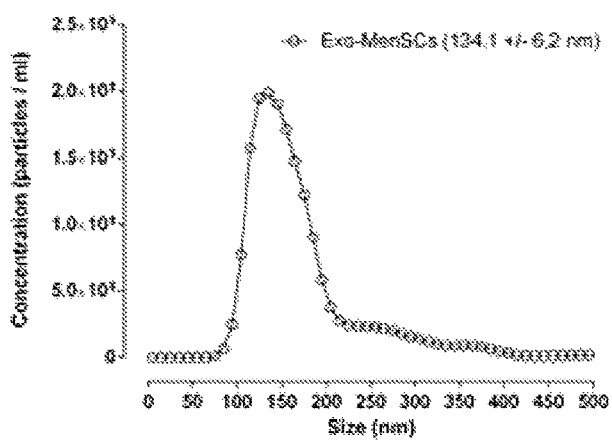
Figure 2:
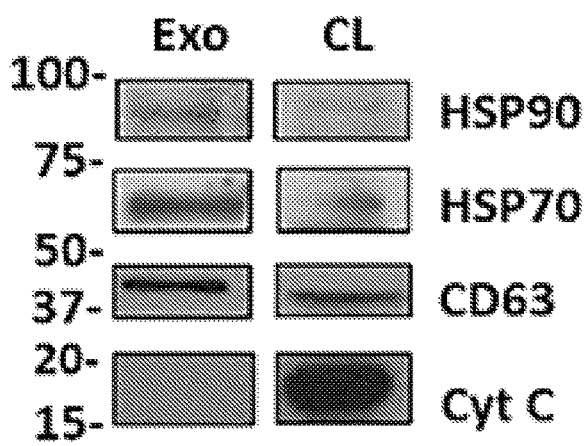

A substantially pure population of Exosomes can be isolated from the supernatant (conditioned media) of the MenSCs culture following serial centrifugation steps, as described in the Examples. As shown in FIG. 2, the substantially pure population of exosomes obtained from MenSCs showed a typical round-shaped appearance and size of ~94±2 nm and a size measured by nanoparticle tracking analysis (NTA) was ~134.1±6.2 nm. In accordance with previous reports, immunoblotting showed positive expression of HSP90, HSP70 and CD63, which were enriched in comparison with the cell lysate, while the mitochondrial markers cytochrome C was absent in the purified exosome fraction.

The present invention is based on the discovery that the substantially pure population of exosomes isolated from a culture of MenSCs have anti-angiogenic properties and can be used to treat a disease with increased pro-angiogenic activity such as, or selected from the list consisting of cancer, multiple sclerosis, vascular malformations, obesity, psoriasis, warts, allergic dermatitis, kaposi's sarcoma in AIDS, diabetic retinopathy, primary pulmonary hypertension, asthma, cystic fibrosis, inflammatory bowel disease, periodontal disease, liver cirrhosis, endometriosis, ovarian cysts, uterine bleeding, arthritis, osteomyelitis and diabetic nephropathy.

Angiogenesis refers to the growth of new blood vessels from pre-existing blood vessels. It is characterized by an increase expression of pro-angiogenic factors, such as vascular endothelial growth factor (VEGF), fibroblast growth factor (FGF), NFKB, HIF1α and ROS. VEGF is a potent pro-angiogenic factor and NFKB has been shown to be involved in the up-regulation of VEGF (Inhibition of NF-kappaB activity decreases the VEGF mRNA expression in MDA-MB-231 breast cancer cells). ROS is also essentially required to induce physiological angiogenesis, but uncontrolled, continuous ROS production promotes pathological angiogenesis operating mainly on the VEGF signaling pathway and HIF1-α has also been shown to regulate VEGF. Therefore, inhibitors of any of these factors might be useful to treat diseases with increased pro-angiogenesis. In this sense, we herein show that a substantially pure population of exosomes derived from or obtained from a culture of MenSCs decreased VEGF expression at the mRNA and/or protein level in different cell types and FGF in PC3 cancer cells (FIG. 4, 10A-B). We also showed that a substantially pure population of exosomes can inhibit ROS (FIG. 5, FIG. 10D-E) and NFKB activity (FIG. 4D) and HIF1α (FIG. 8) in different cell types. Consequently, the invention has the clear potential to reduce angiogenesis in different environments and therefore to be used to treat different diseases related with angiogenesis, in particular for the treatment of cancer since angiogenesis plays a crucial role in cancer.

To our knowledge, this is the first time that a substantially pure population of exosomes derived from MenSCs are shown to have a specific therapeutic effect in angiogenesis and thus, it is a first aspect of the present invention to provide a composition comprising a substantial pure population of exosomes obtained or obtainable by Menstrual Stem cells (MenSCs), for use in therapy.

It is noted that, in the context of the present invention the MenSCs are characterized by expressing CD105, CD44, CD73, CD90 and HLAABC, and do not express CD45, CD34, CD14 and HLA-DR. It is further noted that mesodermal lineage induction of the MenSCs showed positive specific staining for fat, bone and cartilage differentiation, and that MenSCs are obtained from menstrual fluid from fertile healthy woman donors aged 13 to 50 years old, preferably 19 to 45 years old, more preferably between 20 and 40 years old. It is still further noted that the MenSCs of the present invention are strictly non-embryonic derived stem cells.

In addition, the substantially pure population of exosomes referred to throughout the present invention, are characterized by a round-shape of 30 to 200 nm, preferably 30 to 150 nm, preferably 40 to 120 nm, more preferably between 50 and 100 nm in size and by the expression of HSP90, HSP70 and CD63, and the exosomes are obtained from the MenSCs by well-known techniques. In this sense and just a mere example, the exosomes can be obtained from the MenSCs by following serial centrifugation steps of the MenSCs culture method or, more specifically, by a method which comprises the following steps:

1. Centrifugation of MenSCs cultured in DMEM media and collection of the supernatant.
2. Serial centrifugations of the supernatant (300 g for 10 min, 2000 g for 10 min and 10,000 g for 30 min at 4° C.).
3. Ultracentrifugation of the supernatant at 100,000 g for 70 min at 4° C.
4. Resuspension (in the final excipient of the composition) of the pellet containing the extracellular vesicles enriched in exosomes and centrifugation again at 100,000 g for 1 h at 4° C.
5. Resuspension of the pellet in the final excipient of the composition.

It is a further aspect of the present invention (a second aspect) to provide a safe and more effective preparation or composition of exosomes that is suitable for the treatment of diseases and conditions that involve angiogenic reactions. In this sense, a second aspect of the invention refers to a preparation or composition comprising a substantially pure population of exosomes obtained or derived from MenSCs for use in the treatment of diseases and conditions that involve angiogenic reactions, such as a disease with increased pro-angiogenic activity selected from the list consisting of cancer, multiple sclerosis, vascular malformations, obesity, psoriasis, warts, allergic dermatitis, kaposi's sarcoma in AIDS, diabetic retinopathy, primary pulmonary hypertension, asthma, cystic fibrosis, inflammatory bowel disease, periodontal disease, liver cirrhosis, endometriosis, ovarian cysts, uterine bleeding, arthritis, osteomyelitis and diabetic nephropathy. Other objects of the present invention will become apparent to the person of skill upon studying the present description of the invention. In a preferred embodiment of the second aspect of the invention, the preparation or composition is for use in the treatment of cancer, in particular prostate cancer, preferably hormone refractory prostate cancer, breast cancer, preferably invasive ductal breast cancer or pancreatic cancer.

A third aspect of the invention refers to a pharmaceutical preparation comprising a substantially pure population of MenSCs derived exosomes. The pharmaceutical preparation according to this aspect of the present invention is preferably enriched for exosomes. For this, generally any suitable method for purifying and/or enriching can be used, such as methods comprising magnetic particles, filtration, dialysis, ultracentrifugation, ExoQuick™ (Systems Biosciences, CA, USA), and/or chromatography. Nevertheless, preferred is a method that comprises polyethylene glycol precipitation and/or chromatographically enrichment using the monolithic technology (e.g. CIM®, BIA separations, Austria) as stationary phases instead of columns packed with porous particles. Monoliths are continuous stationary phases that are cast as a homogeneous column in a single piece and prepared in various dimensions with agglomeration-type or fibrous microstructures. (see Iberer, G., Hahn, R., Jungbauer, A. LC-GC, 1999, 17, 998). Using these methods, surprisingly active fractions containing exosomes could be obtained. Then, in order to identify the most suitable fraction according to the invention, fractions being enriched with exosomes are tested for their in vitro anti-angiogenic effect, and can further be analyzed, in microbiological, in virulence and in pyrogen tests to, for example, excluded possible contaminations. In addition, these fractions can be studied with regard to protein content, and particle size.

It could be found that fractions being enriched with exosomes were particularly useful in any of the diseases according to the second aspect of the present invention, if they exhibited strong in vitro anti-angiogenic effects in activity tests, where, following the addition of said exosome-enriched fraction, reduced endogenous levels of ROS in cells and a reduce expression of pro-angiogenic factors such as VEGF, NF-KB, FGF and HIFα, could be found.

The present invention is thus based on the novel concept for an improved prevention and treatment of diseases by using a substantially pure population of MenSCs derived exosomes, in particular in patients suffering from a disease according to the second aspect of the invention.

The pharmaceutical preparation according to the present invention is preferably enriched with exosomes having a size of between about 30 to 200 nm, 30 to 150 nm, preferably 40 to 120 nm, more preferably between 50 and 100 nm in size. "About" shall mean a +/−10% deviation. Further preferred, the substantially pure population of exosomes are positive for cellular exosome markers.

The pharmaceutical composition may contain at least 1 ug of exosomes, preferably between 1 and 40 ug, more preferably between 5 and 35 ug, and even more preferably between 10 and 20 ug of exosomes. The exosome amount can be measured by protein amount, for example, by using a Bradphore assay (BioRad) or a BCA protein assay kit (Pierce). Yet, the optimal dose will be selected according to the administration route, treatment regime and/or administration schedule, having regard to the existing toxicity and effectiveness data. In a preferred embodiment the substantially pure population of exosomes is in a dosage capable of providing an anti-angiogenic effect in the absence of toxic effects. There are insufficient data from human and animal studies to establish a Safe Upper Level for this substantially pure population of exosomes, although the available data from this invention indicates that it is of low toxicity in mice. Accordingly, in the present invention, the dosage of the pharmaceutical composition is not particularly restricted and may vary with the type and size of the tumor, the weight and health of the patient and might be estimated by a person skilled in the art, taking into account the experimental data from this invention, where tumors mainly composed of PC3 cells, of 80 mm3 in mice showed reduced angiogenic properties after treatment with 3 dosis of 10 µg/100 µl of the substantially pure population of MenScs-derived exosomes, 3 times in 3 days intervals.

In addition, said one or more pharmaceutical compositions are formulated to be compatible with its intended route of administration. Methods to accomplish the administration are known to those of ordinary skill in the art. This includes, for example, injections, by parenteral routes such as intratumoral, intravascular, intravenous, intraarterial, subcutaneous, intramuscular, intraperitoneal, intraventricular, intraepidural, or others as well as oral, nasal, ophthalmic, rectal, or topical. Sustained release administration is also specifically contemplated, by such means as depot injections or erodible implants. A preferred route of administration is intratumoral administration, which is herein understood as the administration within the tumor. Alternatively, the administration can be intravascular, which is herein understood as the administration within a vessel or vessels and typically includes intravenous or intraarterial administration.

In another aspect of the present invention, the pharmaceutical preparation according to the present invention, is suitable for i.v. administration, such as for example, intravenous administration or infusion into a patient in need thereof, or for intra-tumoral administration. Another aspect of the present invention then relates to a method for producing a pharmaceutical preparation according to the present invention, comprising the following steps: a) providing a cell culture medium supernatant from MenSCs comprising exosomes, b) enriching substantially pure populations of exosomes, c) preferably determining an in vitro anti-angiogenic and selecting those substantially pure population of exosomes that exhibit an anti-angiogenic effect, and e) admixing said substantially pure population of exosomes of step c) with at least one suitable pharmaceutical excipient and/or carrier.

The method for producing a pharmaceutical preparation according to the present invention comprises the step of specifically enriching for substantially pure populations of exosomes. For this, generally any suitable method for purifying and/or enriching can be used, such as methods comprising magnetic particles, filtration, dialysis, ultracentrifugation, ExoQuick™ (Systems Biosciences, CA, USA), and/or chromatography. Nevertheless, preferred is a method that comprises polyethylene glycol precipitation and/or a monolithic method (see above), since using these methods, surprisingly active fractions containing substantially pure populations of exosomes could be obtained.

Preferred is a method for producing a pharmaceutical preparation according to the present invention, wherein fractions that were enriched for substantially pure populations of exosomes are further analyzed in microbiological tests, virulence tests, protein content, pyrogen tests, and particle size, in order to identify the most suitable fraction according to the invention. It could be found that fractions that were enriched for exosomes were particularly useful in the methods according to the present invention, if they exhibited strong in vitro anti-angiogenic effects in activity tests.

In addition, please find herein the following clauses in connection to the present invention:

1. A composition comprising a substantially pure population of exosomes obtained or obtainable from Menstrual Stem cells (MenSCs), for use in therapy, wherein a substantially pure population refers to a population of extracellular vesicles wherein at least about 75% of the extracellular vesicles are exosomes obtained or obtainable from Menstrual Stem cells (MenSCs).
2. A composition comprising a substantially pure population of exosomes obtained or obtainable from MenSCs, for use in a method of treatment of a disease with increased pro-angiogenic activity selected from the list consisting of cancer, multiple sclerosis, vascular malformations, obesity, psoriasis, warts, allergic dermatitis, kaposi's sarcoma in AIDS, diabetic retinopathy, primary pulmonary hypertension, asthma, cystic fibrosis, inflammatory bowel disease, periodontal disease, liver cirrhosis, endometriosis, ovarian cysts, uterine bleeding, arthritis, osteomyelitis, diabetic nephropathy.
3. The composition for use according to claim 2, wherein the disease is prostate cancer.
4. The composition for use according to claim 3, wherein the disease is hormone refractory prostate cancer.
5. The composition for use according to claim 2, wherein the disease is breast cancer.
6. The composition for use according to claim 5, wherein the disease is invasive ductal breast cancer.
7. The composition for use according to claim 2, wherein the disease is pancreatic cancer.
8. The composition for use according to any of claims 2 to 7, wherein the treatment is administered intra-tumoral.
9. The composition for use according to any of claims 2 to 7, wherein the composition comprises at least 1 µg of exosomes as measured by protein amount.
10. The composition for use according to any of claims 2 to 7, wherein the composition comprises from 1 to 40 µg of exosomes, preferably from 5 to 35 µg of exosomes, more preferably from about 10 to about 20 µg of exosomes as measured by protein amount.
11. A pharmaceutical composition that comprises a substantially pure population of exosomes from MenSCs and optionally a pharmaceutically acceptable carrier and/or excipients, wherein a substantially pure population refers to a population of extracellular vesicles wherein at least about 75% of the extracellular vesicles are exosomes obtained or obtainable from Menstrual Stem cells (MenSCs).
12. The pharmaceutical composition according to claim 11 wherein the excipient is Phosphate buffered saline (PBS).
13. The pharmaceutical composition according to claim 12, wherein said composition further comprises a compound suitable for the treatment of cancer.
14. The pharmaceutical composition according to claim 13, wherein the compound suitable for the treatment of cancer is an antibody such as bevacizumab or ranibizumab.
15. The pharmaceutical composition according to claim 13, wherein the compound suitable for the treatment of cancer is a chemotherapeutic compound such as 5-fluorouracil, cyclophosphamide or Doxorubicin.

The present invention will now be described further in the following examples, nevertheless, without being limited thereto. For the purpose of the present invention, all references as cited are incorporated by reference in their entireties.

EXAMPLES

Materials and Methods
Biological Samples and Cell Culture

This study was revised and approved by the Ethics Committee of the Universidad de los Andes. Menstrual fluids and bone marrow were obtained after informed consents following institutional guidelines from four healthy donors aged 24-38 years-old and two hip-operated patients aged 60-68 years-old, respectively. MSCs were isolated, cultured, and characterized as described previously ("Characterization of menstrual stem cells: angiogenic effect, migration, hematopoietic stem cell support in comparison with bone marrow mesenchymal stem cells". Alcayaga-Miranda F et al., Stem cell research & therapy. 2015; "The immunosuppressive signature of menstrual blood mesenchymal stem cells entails opposite effects on experimental arthritis and graft versus host diseases". Luz-Crawford P et al., Stem cells. 2016; "Combination therapy of menstrual derived mesenchymal stem cells and antibiotics ameliorates survival in sepsis". Alcayaga-Miranda F et al., Stem cell research & therapy. 2015) and cryopreserved at low passage (<5) until use.

Briefly, to obtain and culture MenSCs samples, these were collected in a menstrual silicone cup (Mialuna®, Santiago, Chile) during the earliest days of a menstrual cycle. Menstrual blood samples were transferred into a 50 ml tube with 10 ml phosphate buffered saline (PBS) containing 0.25 mg/ml amphotericin B, penicillin 100 IU, streptomycin 100 mg/ml and 2 mM ethylenediaminetetraacetic acid (EDTA) (all from Gibco, Paisley, UK). Menstrual blood mononuclear cells were separated by Ficoll-Paque Plus (GE Healthcare, Amersham, UK) (1.077 g/ml) density gradient according to the manufacturer's instructions and washed in PBS. Cells were subsequently cultured in a T25 flask (Falcon®, Becton Dickinson, USA) containing (Dulbecco's) modified Eagle's medium (DMEM) high glucose (Gibco) supplemented with 1% penicillin/streptomycin (P/S), 1% amphotericin B, 1% glutamine (Gibco) and 15% fetal bovine serum (FBS) (Lonza, Walkersville, Md. USA) at 37° C., 5% CO2 in order to obtain adherent cells. Media were changed the next day to wash non adherent cells. Cells were seeded again as follows: adherent cells were detached using 0.05% trypsin-EDTA (Gibco), counted and sub-cultured. BMSCs were grown under the same conditions as MenSCs.

Human umbilical vein endothelial cells (HUVEC), human pancreas adenocarcinoma MIA PaCa-2, human pancreas carcinoma PANC-1, metastatic human breast cancer MD-MB-231, metastatic human breast cancer MCF-7, metastatic human prostate adenocarcinoma PC3, metastatic human prostate carcinoma DU 145, metastatic human prostate carcinoma LNCaP and metastatic human prostate cancer VCaP cell lines were obtained from the American Type Culture Collection (ATCC, Manassas, Va., USA). HUVEC were cultured in endothelial growth media (EGM-2, Lonza, USA) with 5% FBS (Lonza, Walkersville, Md. USA), 1% P/S (Life Technologies, Santiago, RM, Chile) and 1% L-glutamine (Life Technologies, Santiago, RM, Chile). MIA PaCa-2, PANC-1, MDA MB 231, PC3 and VCaP cell lines were cultured in DMEM (Gibco, Paisley, USA) with 10% FBS, 1% P/S and 1% L-glutamine. LNCaP, DU 145 and MCF7 cell lines were cultured in RPMI-1640 (Hyclone, GE Healthcare, Utah, USA) with 10% FBS, 1% P/S and 1% L-glutamine. All cells were maintained in a humidified incubator (37° C.; 5% CO2) and routinely tested for the presence of mycoplasma (EZ-PCR Mycoplasma test kit, Biological Industries, Israel Beit-Haemek Ltd).

Immunophenotypic Characterization of MenSCs

Immunophenotyping was performed by fluorescence-activated cell sorting (FACS) using a FACSCanto II cytometer (BD Biosciences, San Jose, Calif., USA) after staining with monoclonal antibodies CD105, CD90, CD73, CD44, HLA-ABC, HLA-DR, CD34 and CD45 (all from BD Pharmingen San Jose, Calif., USA) using standard protocol. In brief, cells were harvested, washed with a cytometry buffer (PBS+0.2% BSA+0.01% Sodium Azide [all from Sigma-Aldrich, St Lois, USA]) and incubated with the specific labelled antibodies in cytometer buffer for 20 min at 4° C. In all experiments, matching isotype antibodies were used as negative controls. In addition, LIVE/DEAD®Fixable dead cell stain kit (Invitrogen) was used to determine the viability cells by flow cytometry according to the manufacturer's protocol. Data (5,000 events) were analyzed on FlowJo Software vX 10.0.7 (Tree star Inc, Stanford).

Exosomes Purification

For purification of exosomes (particles of 30-200 nM diametre), MenSCs ($3*10^7$ cells) at passages 2 to 6 were supplemented with serum-free DMEM (Gibco), 2 mM L-glutamine (Life Technologies, Santiago, RM, Chile) and 1% penicillin/streptomycin (Life Technologies, Santiago, RM, Chile) for 72 h. The supernatant (conditioned media) was collected and subjected to serial centrifugations (300 g for 10 min, 2000 g for 10 min and 10,000 g for 30 min at 4° C.). The supernatant was ultracentrifuged at 100,000 g for 70 min at 4° C. to obtain the pellet, i.e. the exosome-enriched fraction which was washed with 1 ml PBS and centrifuged again at 100,000 g for 1 h at 4° C. The pellet was resuspended in 50 to 100 ul of PBS. Protein concentration was quantified by Bradphore assay (BioRAd, CA, USA) according to standard protocols (other assays equally valid are the BCA protein assay (Pierce). Exosome size and shape were evaluate by electron microscopy (EM) and analyzed using nanoparticles tracking analysis (NTA). Exosomes fractions were characterized by western blot determining the presence of the exosomal marker CD63, HSP70 and CD90. Lysed exosomes were used in all experiments as negative control. Exosomes were lysed with 1% triton X100, incubated with 0.5% trypsin for 30 min at 37° C. and ultracentrifuged at 100000 g for 70 min.

Exosomes Characterization

Exosome size and shape were evaluated by electron microscopy (EM). Briefly, 30 μg exosomes were fixed with 2% PFA and deposited on Formvar-carbon-coated EM grids, and contrasted with uranyl acetate. All the grids were examined with a Philips Tecnai 12 electron microscope operated at 80 kV. Nanoparticle tracking analysis (NTA) were performed using a NanoSight N5500 instrument (NanoSight NTA 2.3 Nanoparticle Tracking and Analysis Release Version Build 0033) following the manufacturer's instructions. Briefly, exosomes fractions were processed in duplicate and diluted with PBS over a range of concentration to obtain between 10 and 100 particles per image. Exosomes samples were mixed before analysis into the chamber and two videos per sample were processed and analyzed to give the mean, mode, and median particle size together with an estimated number of particles.

Exosome markers were identified by Western blot according to previously published methods. In brief, exosomal proteins (15 μg) were separated on a 12% polyacrylamide gel and transferred to polyvinylidene difluoride membrane (PVDF; Thermo Scientific) for 1 hour at 100 V. The membrane was washed in wash buffer (PBS TWEEN 0.1%) three times for 10 min and blocked with 5% skimmed milk in PBS TWEEN (0.1%) for one hour at room temperature under agitation. The blocked membrane was further probed with the previously identified exosome-specific marker anti-CD63 (rabbit polyclonal 1:500; Santa Cruz Biotechnology), anti-heat shock protein 70 (Hsp70, mouse monoclonal 1:500, Stressgen), anti-heat shock protein 90 (Hsp90, rabbit polyclonal 1:500, Stressgen), and anti-cytochrome C (mouse monoclonal 1:1000, BD Bioscience). This was achieved by incubating the membrane in primary antibody diluted in 5% skim milk in PBS TWEEN (0.1%) at 4° C. overnight on the laboratory rocker. After an overnight incubation, the membrane was washed with wash buffer and exposed to the appropriated secondary antibody (goat anti-rabbit HRP or goat anti-mouse HRP; BioRad). The membrane was washed 3 times for 10 min in wash buffer. Blots were revealed by the enhanced chemiluminescence method (Amersham). Protein loading was evaluated by SDS-PAGE followed by silver staining.

Characterization and Internalization Assay

To study the uptake of isolated exosomes, exosomes (20 μg) resuspended in phosphate buffered saline (PBS) were incubated with anti-CD63-FITC (Santa Cruz Biotechnology, CA, USA) or IgG1-FITC (isotype control; Biolegend, CA, USA) overnight at 4° C. The mix was pelleted by ultracentrifugation on a 30% sucrose/D20 density cushion (100,000 g for 70 min at 4° C.) and the immuno-labeled exosomes were purified from the nonbound immunocomplexes. The exosomes interface was recovered and subjected to ultracentrifugation after dilution with PBS. Finally, the pellet containing immunofluorescent-labeled exosomes was resuspended in 200 μL PBS and added to 2×104 PC3 cells for 3 hours at either 37° C. or 4° C. Internalization of exosomes in PC3 cells was determined by fluorescence-activated cell sorting (FACS) (FACS Canto II, BD Biosciences, USA) and visualized with confocal microscopy (FV1200 Laser Scanning Microscope in combination with an IX83 automated inverted microscope platform, Olympus). For FACS analysis, cells were washed twice with PBS before acquisition in the flow cytometer; the data obtained was analyzed with FlowJo Software vX 10.0.7 (Tree star Inc, Stanford). For confocal microscopy, cells were washed twice with PBS and incubated with 2 μM CellTracker™ Red CMTPX (Life Technologies, Carlsbad, Calif.), according to the manufacturer's protocol. Cells were washed in PBS, fixed in 4% paraformaldehyde and mounted in Vectashield (Vector Laboratories Inc., Burlingame, Calif.) with 4,'6'-diaminido-2-phenylindole (DAPI; Bio Rad, USA). Images were taken with a 100× objective of numerical aperture 1.4.

Co-Culture of Cancer Cells with MenSCs or their Exosomes

For exosomes experiments, cancer cells (2×105) were plated in a 6-well plate in complete media for 16 h. Semiconfluent layers of cancer cells were twice washed with PBS and serum-free DMEM was added prior to incubation with 10 μg of exosomes, lysed exosomes and vehicle, at 37° C. for 36 h. Subsequently, the conditioned medium (CM) and cells were collected, and processed for further studies as required. For ROS and angiogenesis in vitro studies, cancer cells were incubated with 10 mM N-acetylcysteine (NAC) (Calbiochem), 250 μM H202 (Merck, Darmstadt, Germany) or exosomes plus H202. For MenSCs co-cultured with cancer cells, PC3 cells (4×106) were grown with MenSCs (2×106) in complete media for 16 h. After two washes with PBS, cells were cocultured with serum-free DMEM for 36 h, then separated by fluorescence-activated cell sorting (FACSAria, BD, USA) using double-staining for CD73-PECy7 and CD90-APC (BD Pharmingen, CA, USA). Sorted PC3 cells CD73−/CD90− were processed for further studies as required.

RNA Expression Analysis by RT-qPCR

Total RNAs were extracted using the RNeasy mini kit (Qiagen, CA, USA) and complementary cDNA was synthesized using 2 µg of RNA in a 20 µl reaction mixture using SuperScript III First-Strand Synthesis for RT-PCR (Invitrogen, Carlsbad, Calif.). RT-qPCR was performed using SYBR GREEN Reagents (Brilliant® II SYBR® Green QPCR Master Mix, Agilent Technologies). All primers sets were previously screened for efficiency and their sequences were VEGF-A (F): 5'ACACATTGTTGGAAGCAGCCC-3' (SEQ ID NO: 1), (R): 5'-AGGAAGGTCAACCACT-CACACACA-3' (SEQ ID NO: 2); bFGF (F): 5'-AGAAGAGCGACCCTCACATCA-3' (SEQ ID NO: 3), (R): 5'-CGGTTAGCACACACTCCTTTG-3' (SEQ ID NO: 4); GAPDH (F): 5'-GGTCTCCTCTGACTTGAACA-3' (SEQ ID NO: 5), (R): 5'-GTGAGGGTCTCTCTCTTCCT-3' (SEQ ID NO: 6). All values were normalized to GAPDH housekeeping gene and expressed as relative expression or fold change using the respective formulae 2-ΔΔCt.

Western Blot Analysis of VEGF

Equal amounts of proteins were resolved by sodium dodecyl sulfatepolyacrylamide gel electrophoresis and blotted, and membranes were first probed with anti-VEGF antibody (rabbit polyclonal 1:2000, Abcam) and reprobed with β-actin antibody (mouse monoclonal 1:1000, Santa Cruz). Goat anti-mouse HRP and goat anti-rabbit HRP (BioRad) were used as secondary antibodies. Western blots were revealed by enhanced chemiluminescence (Amersham). Scanned bands were quantified using ImageJ software Version 1.43 (National Institutes of Health, hypertext transfer protocol secure: //rsb.info.nih.gov/ij/). All Western blot results were evaluated by densitometric scanning, corrected with respect to β-actin expression, and expressed relative to the value obtained with the corresponding control (arbitrarily set as 1). Equal protein loading was assessed by anti-β-actin immunoblotting.

ELISA Assay

Conditioned media from PC3 cells (PC3-CM) treated with exosomes, lysed exosomes or untreated, were collected after 36 hours incubation. For detection of VEGF, CM was concentrated approximately 50 fold using ultracentrifugation units (Amicon Ultra; Millipore, Tullagreen, IRL) with a 3 KDa molecular mass cut-off according to the manufacturer's instructions. VEGF was then detected by ELISA (Human VEGF Duoset; R&D system, Minneapolis, Minn.) according to the manufacturer's recommended protocol.

Luciferase Reporter Assay for NF-kappaB (NF-κB) Activity

PC3 cells were transfected with plasmid DNA using the Lipofectamine 2000 transfection reagent (Invitrogen, CA, USA). Briefly, 3×10$^4$ cells were plated onto each well of 24-well plates. After 24 hours, cells were transfected with NF-kB-luciferase reporter plasmid (1 µg) using Opti-MEM I Reduced Serum Medium (Invitrogen, CA, USA), and 6 hours later the medium was replaced with complete media. Twenty-four hours post transfection, cells were cultured with or without MenSCs-derived exosomes. Cells were cultured for another 24 hours and harvested for a luciferase assay (Promega, Madison, Wis.). In all experiments, activities of firefly luciferase were measured using the Promega Luciferase reporter system, and expressed as relative luciferase light units (RLU). The data was normalized by protein concentration.

ROS Measurement

Reactive oxygen species (ROS) were detected by the DCF method. Briefly, 8×10$^4$ cancer cells were cultured in a 24-well plate overnight. Cells were loaded with 10 µM 2',7'-dichlorofluorescin diacetate (DCFDA; Sigma-Aldrich, St. Louis Mo., USA) with or without 10 µg exosomes for 2 h at 37° C. A positive and negative control were also set up using 10 mM NAC and 250 µM H2O2, respectively. Cells were acquired using a FACS Canto II Flow cytometer and analyzed on FlowJo Software vX 10.0.7.

In Vitro Tube Formation Assay

Matrigel grow factor reduced matrix (250 µl; 354235 BD Bioscience, USA) was added to 24-well plates and allowed to polymerize at 37° C. for 30 minutes. HUVEC cells (6×10$^4$) were resuspended in 250 µl of CM from cancer cells treated with exosomes (−CMEXO), exosomes plus H2O2 (−CMEXO+H2O2), lysed exosomes (−CMLysEXO), NAC (−CM+NAC), or untreated (−CM) before seeded on polymerized matrigel. As negative and positive controls, 250 µl of DMEM and EGM-2 (Lonza, Walkersville, Md.) were used, respectively. After 5 h, tube formation was examined with a phase-contrast microscope and 5 representative images per well were captured using an Olympus U-RFL-T camera. Quantification of tube formation was analyzed using WimTube software (Wimasis GmbH, Munich, Germany).

Animal Studies

All mouse studies were performed at the animal facility of the Universidad de los Andes, in accordance with protocols revised and approved by the Institutional Animal Care and Use Committee of Universidad de los Andes. NOD.Cg-Prkdcscid Il2rgtm1Wjl/SzJ (NSG) mice were purchased from Jackson Laboratories (Bar Harbor, Me., USA).

For matrigel plug assay, 8-week-old mice were randomly divided into 5 groups (n=4-12 plugs per group). All groups were implanted subcutaneously with a mixture of 250 µl of growth factor-reduced matrigel (BD Bioscience, San Jose, Calif., USA) and 4×10$^6$ HUVEC cells previously resuspended in 250 µl of DMEM alone or EGM-2, or the PC3-CM previously treated with exosomes (PC3-CMEXO), lysed exosomes (PC3-CMLysEXO), or untreated (PC3-CM). After 14 days, matrigel plugs were harvested and processed for hemoglobin quantification as previously described ("Chorion Mesenchymal Stem Cells Show Superior Differentiation, Immunosuppressive, and Angiogenic Potentials in Comparison With Haploidentical MaternalPlacental Cells." Gonzalez P L et al., Stem cells translational medicine. 2015). The number of blood vessels was counted using ImageJ software (NIH, Bethesda, Md., USA). For mouse prostate tumor growth, subcutaneous PC3 tumor xenografts were established by injection of 1.5×10$^6$ cells into the flanks of 10-week-old male mice (n=8-14 tumors per group). Once the mean tumor volume reached 80 mm$^3$, mice were intratumorally injected with vehicle (100 pL PBS/tumor) or exosomes (10 µg/100 µL/tumor) or lysed exosomes (10 µg/100 µL/tumor) 3 times with 3-days intervals. Tumor size was recorded every 2- to 3-day intervals and the tumor growth was calculated as previously described ("Osteosarcoma cells as carriers to allow antitumor activity of canine oncolytic adenovirus in the presence of neutralizing antibodies". Alcayaga-Miranda F et al., Cancer gene therapy.2010). After 12 days, tumor samples were recovered, photographed, and weighed. For histopathologic analysis, tumor tissues were fixed with 10% formalin, and CD31, VEGF and FGF immunostaining was performed (CyS Laboratory, Santiago, Chile). Hemoglobin concentration was performed in 20 mg of tumor tissue as previously described ("Chorion Mesenchymal Stem Cells Show Superior Differentiation, Immunosuppressive, and Angiogenic Potentials in Comparison With Haploidentical Maternal Placental Cells". Gonzalez P L et al., Stem cells translational medicine. 2015).

Statistical Analysis

One-way ANOVA followed by Tukey's post-test was used for analysis of multiple comparison groups. Two-tailed Student's unpaired t-test was used to compare two groups. Statistical analyses were performed using GraphPad Prism 5 (GraphPad Software, Inc., San Diego, Calif., USA). The numbers of samples per group (n) are specified in the figure legends.

Statistical significance was set at *$p<0.05$; $p<0.01$; *$p<0.001$.

Example 1

Characterization of MEnSCs and MenSCs-Derived Exosomes

Figure 1:
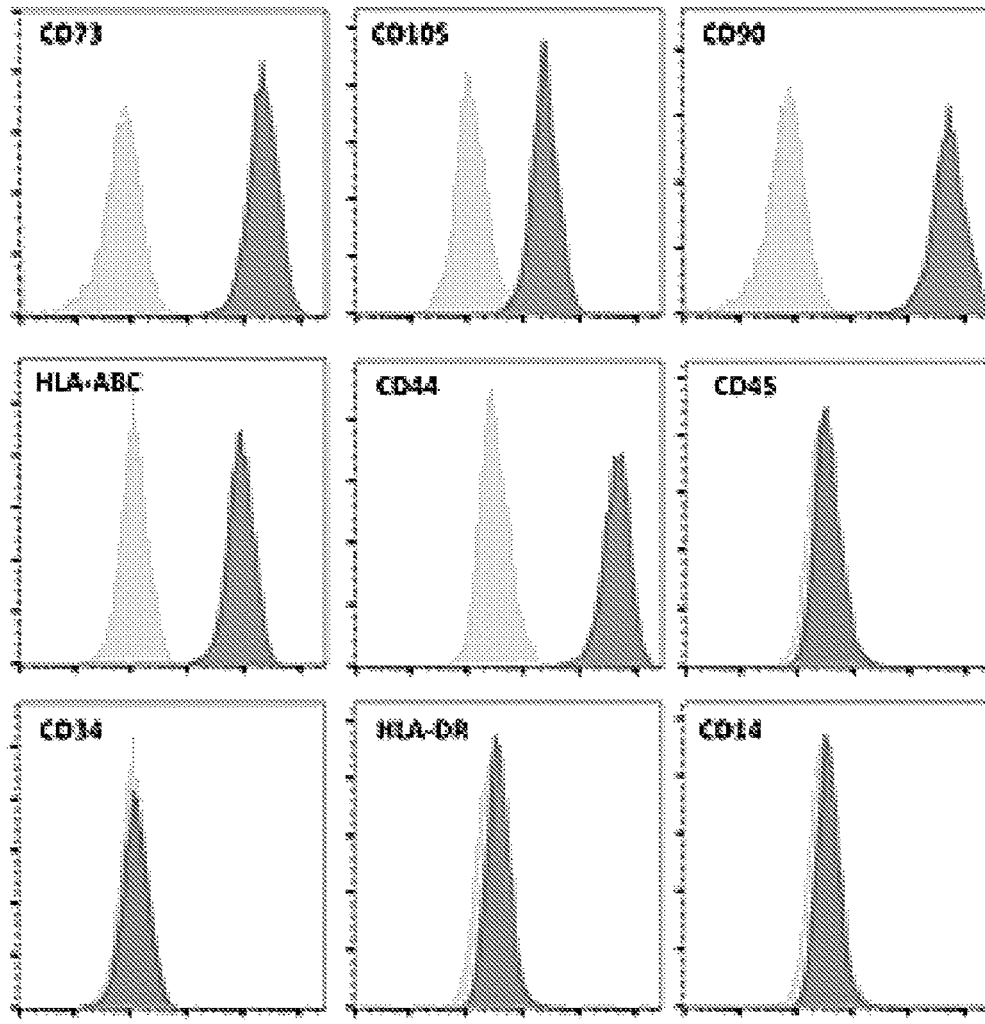
FIG. 1 shows the characterization of MenSCs.
Figure 1:
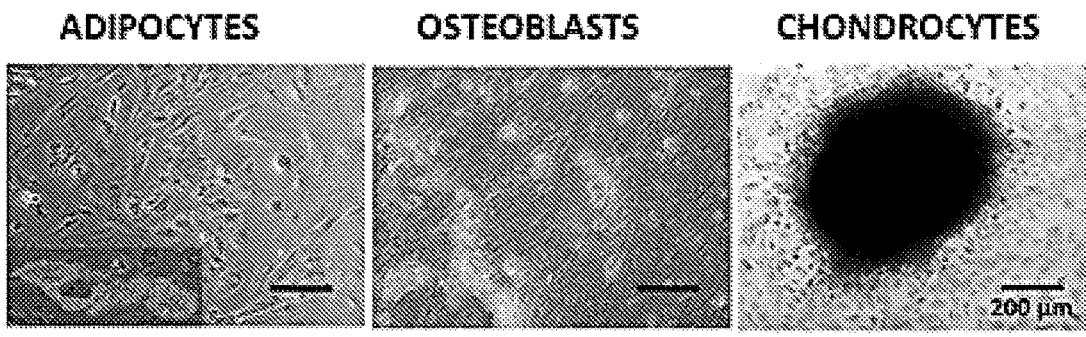

Consistently with previous reports ("Characterization of menstrual stem cells: angiogenic effect, migration, hematopoietic stem cell support in comparison with bone marrow mesenchymal stem cells". Alcayaga-Miranda F et al., Stem cell research & therapy. 2015; "The immunosuppressive signature of menstrual blood mesenchymal stem cells entails opposite effects on experimental arthritis and graft versus host diseases". Luz-Crawford P et al., Stem cells. 2016; "Combination therapy of menstrual derived mesenchymal stem cells and antibiotics ameliorates survival in sepsis". Alcayaga-Miranda F et al., Stem cell research & therapy. 2015; "Endometrial regenerative cells: a novel stem cell Population". Meng X et al., Journal of translational medicine. 2007), MenSCs express CD105, CD44, CD73, CD90 and HLAABC, but showed negative expression for CD45, CD34, CD14 and HLA-DR (FIG. 1A). Also, mesodermal lineage induction showed positive specific staining for fat, bone and cartilage differentiation (FIG. 1B).

Electron microscopy (EM) analysis of the exosomes revealed a typical round-shaped appearance and size of ~94±2 nm (FIG. 2A). The size as measured by nanoparticle tracking analysis (NTA) was ~134.1±6.2 nm (FIG. 2B). In accordance with previous reports, immunoblotting showed positive expression of HSP90, HSP70 and CD63, which were enriched in comparison with the cell lysate, while the mitochondrial markers cytochrome C was absent in the purified exosome fraction (FIG. 2C).

Example 2

Exosomes Uptake by Tumor Cells

The uptake of exosomes by PC3 cells was studied using FACS and confocal microscopy. As shown in FIG. 3 (left panel), anti-CD63-FITC labeled exosomes were localized in the cytoplasm of PC3 cells revealing the internalization of the exosomes. Consistently with other reports ("Interaction and uptake of exosomes by ovarian cancer cells". Escrevente C. et al., BMC cancer. 2011; "Exosome uptake depends on ERK1/2-heat shock protein 27 signaling and lipid Raft-mediated endocytosis negatively regulated by caveolin-1". Svensson K J et al., The Journal of biological chemistry. 2013), no green fluorescence signal was detected after incubation at 4° C., indicating that exosomes internalization by PC3 cells was mediated by an energy-dependent process. The quantification of these data showed that PC3 cells contain 28.25±2.85% of green fluorescent exosomes based on the percentage of max intensity of the population peaks after 3 hours of incubation; meanwhile a decrease in temperature to 4° C. induced a reduction of 98.6±0.005% in the uptake of exosomes by PC3 cells (FIG. 3, right panel).

Example 3

Antiangiogenic Capacity of MEnSCs Exosomes in Prostate Cancer In Vitro

As shown in FIG. 4A, MenSCs-derived exosomes down-regulated the mRNA levels of VEGF and bFGF in PC3 cells ($p<0.001$). This was further confirmed by the reduction of the protein level of VEGF in comparison with untreated cells (FIG. 4B). To confirm the antiangiogenic effect of exosomes, secreted levels of VEGF were determined in the PC3-CM. The lysed exosomes condition was used as control to confirm the exosomes specific effect. Consistently with the downregulation of the VEGF mRNA levels, a ~1.5 fold ($p<0.01$) decrease in VEGF secretion was detected in the PC3-CM treated with MenSCs-derived exosomes. In contrast, the lysed exosomes condition had no effect on the secretion of VEGF, corroborating an exosomes-specific response (FIG. 4C).

As shown in FIG. 4D, exosomes treatment decreased the NF-κB activity compared with untreated PC3 cells ($p<0.05$), while the addition of lysed exosomes had no effect in NF-κB activity. These results indicate that the observed inhibition of NF-κB activity was mediated by exosomes.

Results show that MenSCs-derived exosomes decrease the expression of the pro-angiogenic factors VEGF, NFKB and the mRNA levels of FGF in PC3 prostate cancer cells. A FACS analysis showed that internalization of MenSCs-derived exosomes resulted in decreased ROS production in comparison with the basal expression levels in untreated PC3 cells ($p<0.01$) (FIG. 5A). These reduced levels were comparable to the ROS-inhibitor (NAC) condition. The lysed exosomes showed a reduced effect on ROS expression, suggesting that the ROS modulation was in part mediated by exosomes.

To confirm that the reduction of endogenous ROS in PC3 cells is involved in the inhibition of prostate tumor angiogenesis, the formation of HUVECs into tube like structures on Matrigel was evaluated in the presence of conditioned medium from PC3 cells previously pretreated under 3 different conditions including exosomes treatment (PC3-CMEXO), lysed exosomes treatment (PC3-CMLysEXO) or untreated (PC3-CM) (FIG. 5B).

As expected, in an endothelial growth medium (EGM-2) used as a positive control, HUVECs formed an extensive network of tube-like structures. The tube forming ability was lost when HUVECs were cultured in non-endothelial growth medium (DMEM). As shown in FIG. 5C, image analysis of the tube formation revealed that PC3-CM or PC3-CMLysEXO prompted a more extensive network of tube-like structures in comparison with the PC3-CMEXO or NAC alone. Induction of an oxidative stress through the addition of $H2O2$ treatment to PC3-CMEXO suppressed the antiangiogenic effect of MenSCs-derived exosomes, suggesting that the effect was ROS-dependent. Quantitative analysis of Matrigel assessment was performed by determining percentage of covered area, total loops, total branching points and total tube length in the tube-like structures. As expected, a reduction in all the measured parameters was observed in the PC3-CMEXO group with respect to the PC3-CM group. This effect was reverted in the presence of PC3-CMLysEXO or in the addition of H2O2. Interestingly, quantitative analysis revealed that PC3-CMEXO decreased these angiogenic parameters in almost similar levels as the antioxidant NAC. Overall, results indicate that MenSCs exosomes exert an antiangiogenic effect in vitro in Prostate cancer cells PC3 through the inhibition of the ROS pathway.

MenSCs-derived exosomes were also tested on VCaP, DU145 and LNCaP prostate cancer cell lines. While the exosomes achieved the down regulation of VEGF in VCaP cells at both mRNA and protein levels (FIGS. 6A and B), no effect was detected in DU145 and LNCaP cells. Consequently, DU145-CM previously incubated with MenSCs-derived exosomes (DU145-CMEXO) had no effect in the formation of tube like structures in the matrigel in vitro assay (FIG. 6C), while VCaP-CMEXO showed a strong reduction in the tube-like structures developed in comparison with untreated cells (VCaP-CM). Image analysis in VCaP condition showed a lower percentage of covered area ($p<0.001$), number of loops and branching points ($p<0.01$; $p<0.05$), and smaller tube length ($p<0.05$) after treatment with exosomes. In contrast, LNCaP-CMEXO stimulated an extensive network of tube-like structures in comparison with LNCaP-CM. To determine whether these different observations were mediated by ROS, endogenous ROS levels were determined in the cell lines. The exosomes treatment resulted in a reduction of the ROS level in VCaP cells, while an increase of ROS were determined in LNCaP cells. Unexpectedly, the treatment with MenSCs-exosomes in DU145 cells decreased the endogenous ROS level (FIG. 6D).

Taken together, these data suggest that MenSCs-derived exosomes impact the prostate cancer cells angiogenic effect especially in human refractory prostate cancer cell lines, preferably composed by cells similar to PC3 and/or VcaP cells.

Example 4

Antiangiogenic Capacity of MEnSCs Exosomes in Prostate Cancer In Vivo

Matrigels mixed with HUVECs previously resuspended in the PC3-CM, PC3-CMEXO and PC3-CMLysEXO were implanted into animals (FIG. 7A). For controls, EGM-matrigel and DMEM-matrigel groups were prepared. As expected, profound inhibition of extra and intra-plug angiogenesis were observed in the PC3-CMEXO matrigel group in comparison with the PC3-CM matrigel group; in accordance with previous results, PC3-CMLysEXO partially reverted the anti-angiogenic activity of the exosomes (FIG. 7B). Image analysis reflected that PC3-CMEXO decreased the number of vessels converging toward the implants with respect to PC3-CM ($p<0.001$) and PC3-CMLysEXO ($p<0.05$) (FIG. 7C). In addition, hemoglobin determination in matrigel plugs revealed a reduction in the hemoglobin levels contained in the PC3-CMEXO matrigel group respect to PC3-CM ($p<0.001$) and PC3-CMLysEXO matrigel groups ($p<0.01$) (FIG. 7D).

Results then show that MEnSCs-derived exosomes inhibit angiogenesis of prostate cancer in vivo. To define the effects of MenSCs-derived exosomes on tumor angiogenesis and tumor growth, mice carrying PC3 tumors were injected thrice intratumorally with exosomes, lysed exosomes or vehicle. As expected, an inhibition of extra- and intra-tumor angiogenesis was observed following the exosomes treatment which induced decreased tumor growth with respect to vehicle and lysed exosomes injections ($p<0.05$) (FIG. 8A-B). The quantification of the tissue hemoglobin content revealed a reduction in their level in the exosomes-inoculated group with respect to vehicle ($p<0.05$) and lysed exosomes ($p<0.01$) injections groups (FIG. 8C). The analysis of CD31+ blood vessel in the tumor sections showed a lower vascular density in exosomes-inoculated group in comparison with vehicle ($p<0.001$) and lysed exosomes ($p<0.001$) injection groups (FIG. 8D). HIF-1α, which is regulated at the protein level by oxygen dependent enzymes and, hence, allows for tissue hypoxia detection, showed nuclear positive staining in all the tumor tissues from the three groups but with a less prominent intensity in exosomes-inoculated tumors in comparison with vehicle ($p<0.001$) and lysed exosomes-inoculated tumors ($p<0.01$) (FIG. 8E). This was coupled by a lower positive staining of VEGF positive staining observed in exosomes inoculated tumors in comparison to the vehicle ($p<0.001$) and lysed exosomes-treated ($p<0.01$) tumor sections (FIG. 8F).

These results confirm that MenSCs derived exosomes decrease angiogenesis and also prostate tumor growth in vivo and open up the possibility of providing an efficient way of administration (intra-tumoral administration) of the MEnSCs-derived exosomes for the treatment of prostate cancer.

Example 5

Exosomes Derived from BMSCs, as Opposed to MenSCs Exosomes, Promote Angiogenesis in Prostate Cancer Cells PC3

BMSCs-derived exosomes were isolated and their angiogenic effects on cancer cells assessed. In contrast to MenSC-derived exosomes, the addition of PC3-CM previously incubated with BMSCs-derived exosomes (PC3-CMB-EXO) stimulated the formation of tube-like structures in comparison with the untreated PC3-CM. A higher number of branching points ($p<0.05$), longer tube length ($p<0.05$) and smaller % of covered area ($p<0.01$) were also developed in following treatment with PC3-CMB-EXO with respect to PC3-CM. These results show that BMSCs-derived exosomes promote angiogenesis in vitro, as opposed to MenSC-derived exosomes (FIG. 9A). To confirm the role of ROS in BMSCs-exosomes effect, we determined the endogenous ROS levels in PC3 cells. As shown in FIG. 9B, while BMSCs-exosomes increase the ROS levels in PC3 cells, the lysed exosomes had no effect on ROS production, indicating that ROS modulation was mediated by exosomes. The addition of NAC to the BMSCs-derived exosomes completely inhibited the fluorescent signal, revealing the specificity of the ROS staining. These results show that BMSCs-derived exosomes have a very different effect in angiogenesis than that of exosomes from MenSCs: BMSCs exosomes promote angiogenesis and an increase of ROS expression in prostate cancer cells PC3.

Example 6

MenSCs-Derived Exosomes Reduce the Angiogenesis in Breast Cancer Cells and Pancreatic Cancer Cells To define whether the anti-angiogenic effect of MenSCs-exosomes is cancer type-dependent, mRNA levels of VEGF were also determined in two breast (MDA-MB-231 and MCF-7) and pancreatic (PANC-1 and MiaPaCa-2) cancer cell lines following culture with the exosomes.

As shown in FIG. 10A, MenSCs-exosomes down-regulated the VEGF mRNA levels in breast cancer cell lines ($p<0.001$ MDA-MB-231 and $p<0.05$ MCF-7), and in MIA PaCa-2 cells. Furthermore, exosomes treatment decreased the VEGF protein level in MDA-MB-231 cells, whereas the VEGF level was unchanged in MCF-7 cells. As well, a reduction in VEGF was detected in both pancreatic cancer cell lines (FIG. 10B).

To test the functional effects of these expression changes in the panel of cancer cell lines, an in vitro angiogenesis assay was carried out (FIG. 10C). Consistently with the reduction of VEGF in breast cancer cells, image analysis of tube formation revealed a reduction in the tube-like structures in MDA-MB-231-CMEXO and MCF-7-CMEXO in comparison with untreated cells. As expected, the quantitative analysis revealed that a reduced number of loops and branching points, coupled with lower covered area, and shorter tube length were developed after treatment with MenSCs-derived exosomes. In pancreatic cancer cells, both MIA PaCa-2-CM and MIA PaCa-2-CMEXO showed no effect in the formation of tube-like structures, probably due to the low level of pro-angiogenic factors secreted by MIA PaCa-2 cells ("Phenotype and genotype of pancreatic cancer cell lines". Deer E L et al., Pancreas.2010). However, PANC-1-CMEXO displayed a strong reduction in the formation of tube-like structures respect to PANC-1-CM, indicating that exosomes may reduce angiogenesis in pancreatic cancer cells PANC1.

The reduction of the breast cancer cells angiogenic profiles after treatment with exosomes was related to a reduction in their endogenous ROS levels (FIG. 10D).

In pancreatic cancer, ROS analysis revealed that in PANC-1 cells the treatment with exosomes resulted in a decreased ROS production in comparison with untreated cells. However, in MIA PaCa-2 cells, endogenous ROS levels were unchanged after exosomes treatment (FIG. 10E).

Overall, based on functional assays, MenSCs-derived exosomes have the capacity to reduce angiogenesis of breast cancer cells MDA-MB231-CM and MCF7-CM, and of pancreatic cancer cells PANC1. In these cases it seems to be mediated by a reduction in ROS levels, although the molecular pathway does not seem to be completely clear yet. Regarding MIAPaCa2-CM cells, exosomes were able to reduce the protein levels of VEGF, thus it is clear that exosomes can reduce the angiogenic capacity of these cells as well.

The invention claimed is:

1. A method for treating hormone refractory prostate cancer in a subject, comprising:
   administering, to the subject a composition comprising a pure population of exosomes isolated from stem cells obtained from menstrual fluid (MenSCs).

2. The method of claim 1, wherein the composition is administered intra-tumorally.

3. The method of claim 1, wherein the composition comprises at least about 1 μg of exosomes as measured by the total protein amount contained in the exosomes.

4. The method of claim 3, wherein the composition comprises about 1 to about 40 μg of exosomes of as measured by the total protein amount contained in the exosomes.

5. The method of claim 4, wherein the composition comprises about 5 to about 35 μg of exosomes as measured by the total protein amount contained in the exosomes.

6. The method of claim 5, wherein the composition comprises about 10 to about 20 μg of exosomes as measured by the total protein amount contained in the exosomes.

* * * * *